US011602571B2

(12) United States Patent
Schmitt et al.

(10) Patent No.: US 11,602,571 B2
(45) Date of Patent: Mar. 14, 2023

(54) METHOD OF MANUFACTURING A FRESHENING COMPOSITIONS COMPRISING PARTICLES SUSPENDED IN A STRUCTURED AQUEOUS COMPOSITION

(71) Applicant: The Procter & Gamble Company, Cincinnati, OH (US)

(72) Inventors: Charles L. Schmitt, Cincinnati, OH (US); Carla Jean Colina, Cincinnati, OH (US); Laura Lynn Heilman, Petersburg, KY (US); Steven Anthony Horenziak, Cincinnati, OH (US); Brandon Philip Illie, Felicity, OH (US); Matthew Lawrence Lynch, Mariemont, OH (US); Melinda Phyllis Steffey, Liberty Township, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 71 days.

(21) Appl. No.: 17/315,440

(22) Filed: May 10, 2021

(65) Prior Publication Data

US 2021/0361804 A1 Nov. 25, 2021

Related U.S. Application Data

(60) Provisional application No. 63/026,761, filed on May 19, 2020.

(51) Int. Cl.
*A61L 2/18* (2006.01)

(52) U.S. Cl.
CPC .................................. *A61L 2/18* (2013.01)

(58) Field of Classification Search
CPC .......... A61L 2/18; A61L 2209/21; A61L 2/22; A61L 9/14; A61L 2202/26; A61L 9/012; C11B 9/00; D06M 13/005; D06M 23/02; D06M 23/12
See application file for complete search history.

(56) References Cited

U.S. PATENT DOCUMENTS

| 6,464,384 | B2 * | 10/2002 | Kubera | ............. | B01F 23/23341 |
| | | | | | 366/264 |
| 10,076,583 | B2 * | 9/2018 | Lynch | ...................... | B01J 13/02 |
| 10,080,814 | B2 * | 9/2018 | Lynch | ...................... | B01J 13/00 |

(Continued)

OTHER PUBLICATIONS

Acticide MBS Information Sheet (2013) (Year: 2013).*

(Continued)

*Primary Examiner* — Pamela H Weiss
(74) *Attorney, Agent, or Firm* — Abbey Alicia Lopez; George H. Leal

(57) ABSTRACT

A method of manufacturing an aqueous freshening composition having a plurality of particles suspended by a structurant system is provided. The method includes the steps of: mixing an aqueous carrier and at least 80 wt. % of ion-forming water-soluble ingredients of the freshening composition to form an aqueous premix; subsequently mixing a first polysaccharide into the aqueous premix; mixing a second polysaccharide into the aqueous premix after mixing the first polysaccharide into the aqueous premix to form a structured aqueous composition; and dispersing a plurality of particles into the structured aqueous composition to form the freshening composition.

20 Claims, 2 Drawing Sheets

(56) References Cited

U.S. PATENT DOCUMENTS

| | | | | |
|---|---|---|---|---|
| 10,143,764 B2* | 12/2018 | Lynch | ............ | A61L 2/22 |
| 10,888,633 B2 | 1/2021 | Lynch et al. | | |
| 11,097,031 B2* | 8/2021 | Lynch | ............ | A61K 8/73 |
| 2013/0123166 A1* | 5/2013 | Gizaw | ............ | C11D 3/3776 |
| | | | | 510/515 |
| 2018/0028706 A1* | 2/2018 | Lynch | ............ | B01J 13/02 |
| 2018/0028707 A1* | 2/2018 | Lynch | ............ | A61L 9/14 |
| 2018/0028708 A1* | 2/2018 | Lynch | ............ | A61L 9/14 |
| 2018/0154033 A1* | 6/2018 | Lynch | ............ | A61K 8/416 |
| 2019/0001013 A1 | 1/2019 | Lynch | | |
| 2020/0281840 A1* | 9/2020 | Lynch | ............ | A61K 8/062 |
| 2022/0226225 A1* | 7/2022 | Lynch | ............ | A61K 8/73 |

OTHER PUBLICATIONS

PCT Search Report and Written Opinion for PCT/US2021/031207 dated Aug. 30, 2021, 16 pages.

Higiro et al. "Rheological study of xanthan and locust bean gum interaction in dilute solution: Effect of salt", Food Research International, Elsevier, Amsterdam, NL, vol. 40, No. 4 dated Mar. 23, 2007, pp. 435-447. XP005935434, ISSN: 0963-9969.

\* cited by examiner

METHOD OF MANUFACTURING A FRESHENING COMPOSITIONS COMPRISING PARTICLES SUSPENDED IN A STRUCTURED AQUEOUS COMPOSITION

FIELD

The present disclosure relates to methods of manufacturing freshening composition comprising suspended particles, and, more particularly, to manufacturing freshening composition comprising a polysaccharide structurant system and suspended particles.

BACKGROUND

There is a continued demand for long-lasting and/or controlled freshness on surfaces and in the air. Various different product forms exist to deliver freshness to surfaces, such as clothing and furniture, and to the air. For example, freshness products may take the form of candles, sprays, manual, automatic, and passive air freshener dispensers, laundry detergents, laundry enhancers, and dryer sheets, and various other forms. Sprayable compositions exist that attempt to deliver long-lasting freshness with relatively high levels of perfumes to mask or react with malodors, malodor counteractants that trap or react with malodors, and/or pro-perfumes. Various laundry products exist on the market that incorporate benefit delivery particles, such as encapsulated perfume particles for controlled release of perfume. Encapsulating the perfume provides delayed release of the perfume until the capsule breaks upon movement, such as being rubbed by a hand or across a fabric. Therefore, the perfume capsules can release perfume days or weeks after the perfume capsules are delivered to the fabric or surface.

Attempts have been made to provide sprayable compositions comprising suspended perfume capsules because sprayable compositions provide a way for a user to quickly and easily apply a freshening composition to a particular surface. Manufacturing of freshening composition is best done at large scale, as measured in volume or weight per unit time, to meet commercial goals. For this reason, it is common to manufacture freshening compositions in tanks containing metric tons of material or in devices that produce metric tons per hour. One skilled in the art recognizes that manufacturing at large scales may require very different making steps and mixing profiles than at small scales. It has been found that known methods of making freshening compositions may be ineffective at making large, commercial-scale quantities of the freshening composition. Therefore, there is a need to provide a large-scale, commercial method of manufacturing freshening compositions having suspended particles.

SUMMARY

"Combinations"
A. A method of manufacturing an freshening composition, the method comprising the steps of:
  mixing an aqueous carrier and at least 80 wt. % of ion-forming water-soluble ingredients of the freshening composition to form an aqueous premix;
  subsequently mixing a first polysaccharide into the aqueous premix;
  mixing a second polysaccharide into the aqueous premix after mixing the first polysaccharide into the aqueous premix to form a structured aqueous composition; and
  dispersing a plurality of particles into the structured aqueous composition to form the freshening composition.

B. The method of Paragraph A further comprising the steps of: mixing the first polysaccharide with water to form a first polysaccharide premix prior to the step of mixing the first polysaccharide into the aqueous premix; and mixing the second polysaccharide with water to form a second polysaccharide premix prior to the step of mixing the second polysaccharide into the aqueous premix.

C. The method of Paragraph A or Paragraph B further comprising the step of introducing a portion of the ion-forming water-soluble ingredients into the structured aqueous composition to lower the viscosity of the structured aqueous composition.

D. The method of any of Paragraphs A through C, wherein the aqueous premix, structured aqueous composition, and freshening composition are maintained at a temperature not exceeding 40° C.

E. The method of Paragraph D, wherein the first and second polysaccharide premixes are maintained at a temperature not exceeding 40° C.

F. The method of any of Paragraphs A through E, wherein the ion-forming water-soluble ingredients are selected from the group consisting of: malodor counteractants, acid buffers, preservatives, salts, and combinations thereof.

G. The method of any of Paragraphs A through F further comprising the step of adjusting the pH of the aqueous premix to no more than 7 prior to the step of subsequently mixing a first polysaccharide into the aqueous premix.

H. The method of any of Paragraphs A through G, wherein the first polysaccharide is xanthan gum, and wherein the second polysaccharide is selected from the group consisting of glucomannan including glucomannan from konjac, locust bean gum, tara gum, and combinations thereof.

I. The method of Paragraph H wherein the plurality of particles comprises a plurality of benefit agent delivery particles having a benefit agent and a wall material encapsulating the benefit agent, wherein the benefit agent comprises a material selected from the group consisting of: a perfume mixture, a malodor counteractant, an antimicrobial agent, an insect repellant, and combinations thereof.

J. The method of any of Paragraphs A through I, wherein the method produces greater than 100 Kg hr-1 of freshening composition.

K. The method of any of Paragraphs A through J, wherein the method is selected from the group consisting of a continuous process, a batch process, or combinations thereof.

L. A method of manufacturing an freshening composition, the method comprising the steps of:
  mixing the aqueous carrier and water-soluble ingredients of the freshening composition that comprise a high ionic strength to form an aqueous premix;
  subsequently mixing a first polysaccharide into the aqueous premix to form a first structured composition;
  mixing a second polysaccharide into the aqueous premix after mixing the first polysaccharide into the aqueous premix to form a second structured composition having a yield stress in the range of greater than 0 to about 2,000 mPa and a viscosity in the range of about 2 mPa-s to about 100 mPa-s; and
  dispersing a plurality of particles into the structured aqueous composition to form the freshening composition.

M. The method of Paragraph L further comprising the step of supplying additional shear energy to the freshening composition, wherein the freshening composition is reduced to a viscosity in the range of about 1 mPa-s to about 20 mPa-s and a yield stress in the range of greater than 0 to about 500 mPa.

N. The method of Paragraph L or Paragraph M further comprising the step of introducing a portion of the ion-forming water-soluble ingredients into the freshening composition, wherein the freshening composition is reduced to a viscosity in the range of about 1 mPa-s to about 20 mPa-s and a yield stress in the range of greater than 0 to about 500 mPa.

O. The method of any of Paragraphs L through N, the aqueous premix, structured aqueous composition, and freshening composition are maintained at a temperature not exceeding 40° C.

P. The method of any of Paragraphs L through O further comprising the step of adjusting the pH of the aqueous premix to no more than 5 prior to the step of subsequently mixing a first polysaccharide into the aqueous premix.

Q. The method of any of Paragraphs L through P, wherein the first polysaccharide is xanthan gum, and wherein the second polysaccharide is selected from the group consisting of glucomannan including glucomannan from konjac, locust bean gum, tara gum, and combinations thereof.

R. The method of any of Paragraphs L through Q, wherein the method produces greater than 100 Kg hr-1 of freshening composition, and wherein the method is selected from the group consisting of a continuous process, a batch process, or combinations thereof.

S. A method of manufacturing a freshening composition, the method comprising the steps of:
  mixing an aqueous carrier and ion-forming water-soluble ingredients of the freshening composition in a mix tank, wherein the mix tank comprises:
    a plurality of baffles, wherein the baffles are defined by a baffle width, an impeller having a plurality of blades, wherein the blades are defined by an impeller width, and a particle injector, wherein the impeller width is about 0.3 to about 0.6 times the tank diameter, wherein the mix tank is defined by a tank height and a tank diameter, wherein the tank height is about 0.8 to about 2.0 times the tank diameter, and wherein the baffle width is about 0.05 to about 0.2 times the impeller width,
  subsequently mixing a first polysaccharide into the aqueous premix;
  mixing a second polysaccharide into the aqueous premix after mixing the first polysaccharide into the aqueous premix to form a structured aqueous composition;
    introducing a plurality of particles adjacent the blades of the impeller to form the freshening composition.
T. The method of Paragraph S, wherein either the mix tank comprises a high shear rotor stator mixer in the interior of the mix tank or a static mixer is disposed in the exterior of the mix tank.

DETAILED DESCRIPTION

Figure 1:
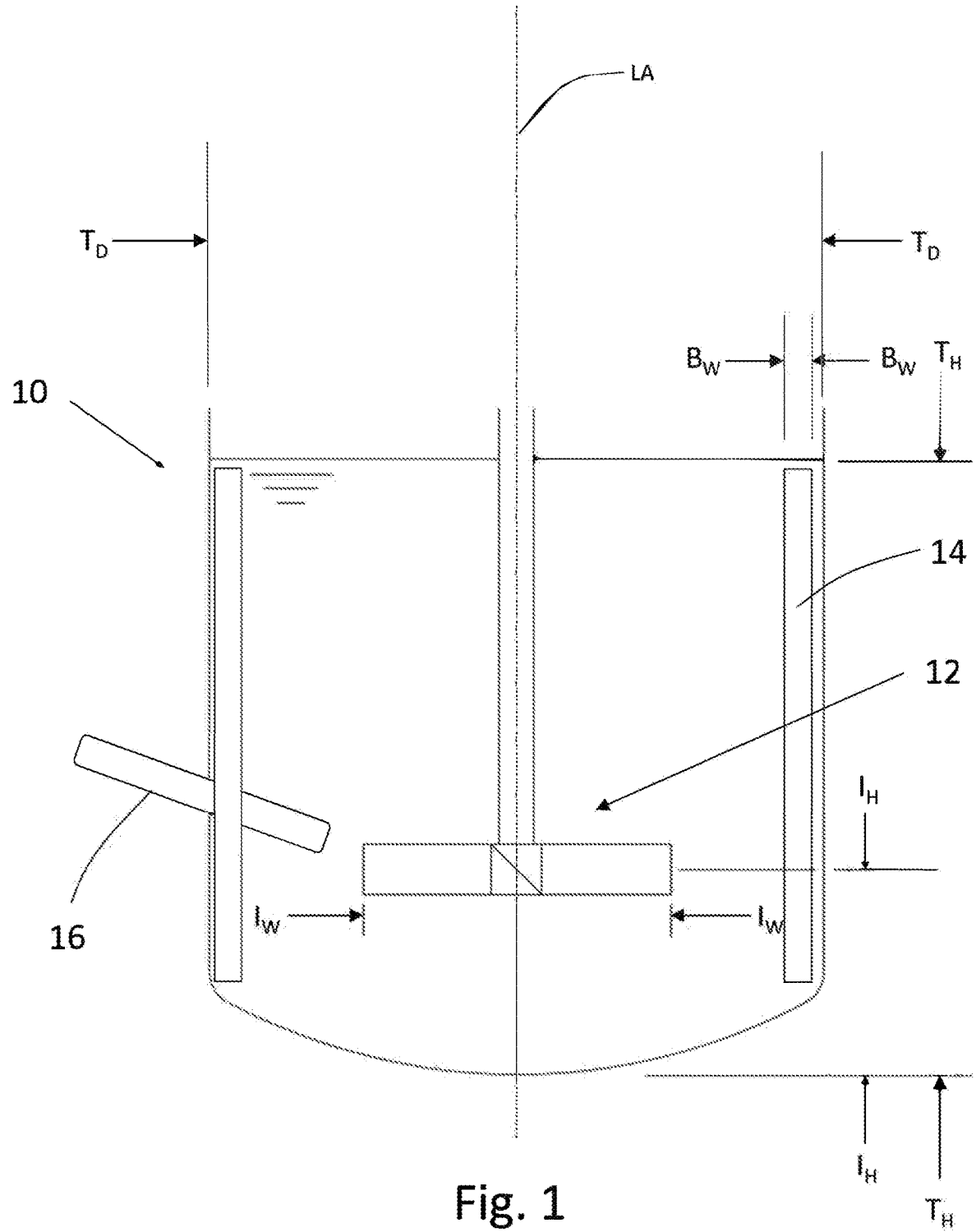
FIG. 1 is a sectional, schematic view of a mix tank of the present invention.

Freshening compositions made by the method of manufacturing of the present invention include a plurality of particles and a structurant system to suspend the particles. The freshening compositions are sprayable and the particles remain suspended for extended periods of time, eliminating the need to shake the product vigorously before use.

The structurant system may be in the form of a polysaccharide system. The polysaccharide system may include a first polysaccharide and a second polysaccharide. The first polysaccharide comprises xanthan gum. The second polysaccharide is selected from the group consisting of: konjac gum, locust bean gum, tara gum, and combinations thereof. The polysaccharide system is well suited for this application as it suspends particles at very small concentrations, resulting in a stable freshening composition with minimal to no residue.

The particles may be in the form of benefit agent delivery particles. The benefit agent delivery particles may include a wall material that encapsulates a benefit agent. A benefit agent may be in the form of a perfume mixture. As used herein, "perfume mixture" comprises at least two perfume raw materials.

Manufacturing of freshening composition is best done at large scale, as measured in volume or weight per unit time, to meet commercial goals. The order of addition of ingredients in the composition, input shear and resulting rheological properties of the fluids affect the manufacturing of freshening compositions at large scale.

The method of manufacturing of the present invention includes first mixing an aqueous carrier and at least 80 wt. % of ion-forming water-soluble ingredients of the freshening composition to form an aqueous premix. After mixing the ion-forming water-soluble ingredients in water, a first polysaccharide is mixed into the aqueous premix. Subsequently, a second polysaccharide is mixed into the aqueous premix to form a structured aqueous composition. Once the two polysaccharides are combined, a polymer network is formed that is capable of suspending a plurality of particles. Once the structured aqueous composition is formed, then a plurality of particles are dispersed into the structured aqueous composition to form the freshening composition. Further processing may include reducing the viscosity of the freshening composition to a viscosity that is sprayable from a spray dispenser.

The method of manufacturing of the present invention may include a batch process or processes, a continuous process or processes, and combinations thereof.

Before adding the plurality of particles to the structured aqueous composition, it may be beneficial to maintain the yield stress of the structured aqueous composition in the range of greater than 0 to about 2,000 millipascals (mPa) and/or a viscosity in the range of about 2 millipascal-seconds (mPa-s) to about 100 mPa-s in order to reduce the amount of mixing energy required to disperse the plurality of particles. Viscosity and yield stress are measured according to the RHEOLOGY TEST METHOD disclosed herein. The greater the mixing energy required to disperse the plurality of particles, the increased chance of negatively impacting the polymer network resulting from the first and second polysaccharides.

Freshening Composition

Freshening compositions of the present disclosure include a plurality of particles and a structurant system to suspend the particles.

The freshening composition may have an ionic strength of less than about 0.02 mol/L. Ionic strength is measured according to the following formula:

$$I = \frac{1}{2}\sum_{i=1}^{n} c_i z_i^2$$

where $c_i$ is equal to the molar concentration of ions, i, and had the units mol/L, and
where $z_i^2$ is equal to the charge number of the ion. See *Basic Physical Chemistry*, Walter J. Moore, p. 370 (1983).

Particles

The freshening composition may include a plurality of particles. As used herein, a "particle" comprises at least a portion of a solid or semi-solid material. The particle may take various different forms. The particles may be 100 wt. % solid or may be hollow. The particle may include, for example, mesoporous particles, activated carbon, zeolites, benefit agent delivery particle, wax, hydrogel, and/or ground nutshells. Preferably, the particle may include a benefit agent delivery particle.

The plurality of particles may have an average longest projected dimension in the range of about 0.1 microns to about 500 microns, alternatively about 1 microns to about 100 microns, alternatively about 5 microns to about 50 microns, alternatively less than 100 microns. The longest projected dimension of any single particle within the plurality of particles is taken as the length of the longest linear dimension that can be inscribed entirely within the outer perimeter of the single particle. The average longest projected dimension of the plurality of particles may be taken as the average of the longest linear dimension that can be inscribed entirely within the single particle, across all the particles within the plurality of particles. It would be appreciated by one of ordinary skill in the art that this average may also be reflected by taking the average across a statistically relevant sample of particles from the plurality of particles.

As discussed above, the freshening composition may include a particle in the form of a benefit agent delivery particle. The benefit agent delivery particle may include a wall material that encapsulates a benefit agent. Benefit agent may be referred herein as a "benefit agent" or an "encapsulated benefit agent". The benefit agent may be selected from the group consisting of: a perfume mixture, an insect repellent, a malodor counteractant, and combinations thereof. In one aspect, the perfume delivery technology may comprise benefit agent delivery particles formed by at least partially surrounding a benefit agent with a wall material. The benefit agent may include materials selected from the group consisting of perfume raw materials such as 3-(4-t-butylphenyl)-2-methyl propanal, 3-(4-t-butylphenyl)-propanal, 3-(4-isopropylphenyl)-2-methylpropanal, 3-(3,4-methylenedioxyphenyl)-2-methylpropanal, and 2,6-dimethyl-5-heptenal, alpha-damascone, beta-damascone, gamma-damascone, beta-damascenone, 6,7-dihydro-1,1,2,3,3-pentamethyl-4(5H)-indanone, methyl-7,3-dihydro-2H-1,5-benzodioxepine-3-one, 2-[2-(4-methyl-3-cyclohexenyl-1-yl)propyl]cyclopentan-2-one, 2-sec-butylcyclohexanone, and beta-dihydro ionone, linalool, ethyllinalool, tetrahydrolinalool, and dihydromyrcenol; silicone oils, waxes such as polyethylene waxes; essential oils such as fish oils, jasmine, camphor, lavender; skin coolants such as menthol, methyllactate; vitamins such as Vitamin A and E; sunscreens; glycerine; catalysts such as manganese catalysts or bleach catalysts; bleach particles such as perborates; silicon dioxide particles; antiperspirant actives; cationic polymers and mixtures thereof. Suitable benefit agents can be obtained from Givaudan Corp. of Mount Olive, N.J., USA, International Flavors & Fragrances Corp. of South Brunswick, N.J., USA, or Firmenich Company of Geneva, Switzerland. As used herein, a "perfume raw material" refers to one or more of the following ingredients: fragrant essential oils; aroma compounds; pro-perfumes; materials supplied with the fragrant essential oils, aroma compounds, and/or pro-perfumes, including stabilizers, diluents, processing agents, and contaminants; and any material that commonly accompanies fragrant essential oils, aroma compounds, and/or pro-perfumes.

The wall material of the benefit agent delivery particle may comprise: melamine, polyacrylamide, silicones, silica, polystyrene, polyurea, polyurethanes, polyacrylate based materials, polyacrylate esters based materials, gelatin, styrene malic anhydride, polyamides, aromatic alcohols, polyvinyl alcohol and mixtures thereof. The melamine wall material may comprise melamine crosslinked with formaldehyde, melamine-dimethoxyethanol crosslinked with formaldehyde, and mixtures thereof. The polystyrene wall material may comprise polyestyrene cross-linked with divinylbenzene. The polyurea wall material may comprise urea crosslinked with formaldehyde, urea crosslinked with gluteraldehyde, polyisocyanate reacted with a polyamine, a polyamine reacted with an aldehyde and mixtures thereof. The polyacrylate based wall materials may comprise polyacrylate formed from methylmethacrylate/dimethylaminomethyl methacrylate, polyacrylate formed from amine acrylate and/or methacrylate and strong acid, polyacrylate formed from carboxylic acid acrylate and/or methacrylate monomer and strong base, polyacrylate formed from an amine acrylate and/or methacrylate monomer and a carboxylic acid acrylate and/or carboxylic acid methacrylate monomer, and mixtures thereof.

The polyacrylate ester-based wall materials may comprise polyacrylate esters formed by alkyl and/or glycidyl esters of acrylic acid and/or methacrylic acid, acrylic acid esters and/or methacrylic acid esters which carry hydroxyl and/or carboxy groups, and allylgluconamide, and mixtures thereof.

The aromatic alcohol-based wall material may comprise aryloxyalkanols, arylalkanols and oligoalkanolarylethers. It may also comprise aromatic compounds with at least one free hydroxyl-group, especially preferred at least two free hydroxy groups that are directly aromatically coupled, wherein it is especially preferred if at least two free hydroxygroups are coupled directly to an aromatic ring, and more especially preferred, positioned relative to each other in meta position. It is preferred that the aromatic alcohols are selected from phenols, cresoles (o-, m-, and p-cresol), naphthols (alpha and beta-naphthol) and thymol, as well as ethylphenols, propylphenols, fluorphenols and methoxyphenols.

The polyurea based wall material may comprise a polyisocyanate. The polyisocyanate may be an aromatic polyisocyanate containing a phenyl, a toluoyl, a xylyl, a naphthyl or a diphenyl moiety (e.g., a polyisocyanurate of toluene diisocyanate, a trimethylol propane-adduct of toluene diisocyanate or a trimethylol propane-adduct of xylylene diisocyanate), an aliphatic polyisocyanale (e.g., a trimer of hexamethylene diisocyanate, a trimer of isophorone diisocyanate and a biuret of hexamethylene diisocyanate), or a mixture thereof (e.g., a mixture of a biuret of hexamethylene diisocyanate and a trimethylol propane-adduct of xylylene diisocyanate). In still other embodiments, the polyisocyante may be cross-linked, the cross-linking agent being a polyamine (e.g., diethylenetriamine, bis(3-aminopropyl) amine, bis(hexanethylene)triamine, tris(2-aminoethyl) amine, triethylenetetramine, N,N'-bis(3-aminopropyl)-1,3-propanediamine, tetraethylenepentamine, pentaethylenehexamine, branched polyethylenimine, chitosan, nisin, gelatin, 1,3-diaminoguanidine monohydrochloride, 1,1-dimethylbiguanide hydrochloride, or guanidine carbonate).

The polyvinyl alcohol based wall material may comprise a crosslinked, hydrophobically modified polyvinyl alcohol, which comprises a crosslinking agent comprising i) a first dextran aldehyde having a molecular weight of from 2,000 to 50,000 Da; and ii) a second dextran aldehyde having a molecular weight of from greater than 50,000 to 2,000,000 Da.

The perfume benefit agent delivery particle may be coated with a deposition aid, a cationic polymer, a non-ionic polymer, an anionic polymer, or mixtures thereof. Suitable polymers may be selected from the group consisting of: polyvinylformaldehyde, partially hydroxylated polyvinylformaldehyde, polyvinylamine, polyethyleneimine, ethoxylated polyethyleneimine, polyvinylalcohol, polyacrylates, and combinations thereof. The freshening composition may include one or more types of benefit agent delivery particles, for examples two benefit agent delivery particles types, wherein one of the first or second benefit agent delivery particles (a) has a wall made of a different wall material than the other; (b) has a wall that includes a different amount of wall material or monomer than the other; or (c) contains a different amount perfume oil ingredient than the other; (d) contains a different perfume oil; (e) has a wall that is cured at a different temperature; (f) contains a perfume oil having a different c Log P value; (g) contains a perfume oil having a different volatility; (h) contains a perfume oil having a different boiling point (i) has a wall made with a different weight ratio of wall materials; (j) has a wall that is cured for different cure time; and (k) has a wall that is heated at a different rate.

Preferably, the perfume benefit agent delivery particle has a wall material comprising a polymer of acrylic acid or derivatives thereof and a benefit agent comprising a perfume mixture.

The freshening composition may comprise any amount of particles. With regard to benefit agent delivery particles, the freshening composition may contain from about 0.001 wt. % to about 2.0 wt. %, by weight of freshening composition, of benefit agent contained with the wall material of the benefit agent delivery particle. Or, the freshening composition may contain from about 0.01 wt. % to about 1.0 wt. %, or most preferably from about 0.05 wt. % to about 0.5 wt. %, by weight of freshening composition, of benefit agent contained within the wall material of the benefit agent delivery particle.

With regard to unencapsulated perfume, the freshening composition may include from about 0.001 wt. % to about 2.0 wt. %, or from about 0.01 wt. % to about 1.0 wt. %, or most preferably from about 0.05 wt. % to about 0.5 wt. %, by weight of freshening composition, of unencapsulated perfume.

Structurant System

The freshening composition includes a structurant system having at least one structuring agent. The structuring agent may include one or more biopolymers. Non-limiting examples of such biopolymers include polysaccharides such as polymers of glucose, fructose, galactose, mannose, rhamnose, glucuronic acid and mixtures thereof.

The structurant system may be in the form of a polysaccharide system. Preferable polysaccharides include xanthan gum, glucomannan, galactomannan, and combinations thereof. The glucomannan may be derived from a natural gum such as konjac gum. The galactomannan may be derived from natural gums such as locust bean gum and/or tara gum Polysaccharides may also include carrageenan. The polysaccharide(s) may be modified such as by deacetylation.

The freshening composition may include a polysaccharide system comprising at least two polysaccharides, such as a first polysaccharide and a second polysaccharide. The first polysaccharide may be xanthan gum. The second polysaccharide may be selected from the group consisting of glucomannan, galactomannan, and combinations thereof. The second polysaccharide may be selected from the group consisting of konjac gum, locust bean gum, tara gum, and combinations thereof.

Preferably, the first polysaccharide is xanthan gum and the second polysaccharide is konjac gum.

The first polysaccharide may be present at a level of greater than 10 wt. % and less than 90 wt %, alternatively about 20 wt. % to about 80 wt. %, alternatively about 40 wt. % to about 60 wt. %, by weight of the polysaccharide system.

The second polysaccharide may be present at a level of about 15 wt. % to about 85 wt. %, alternatively about 20 wt. % to about 80 wt. %, alternatively about 40 wt. % to about 60 wt. %, by weight of the polysaccharide system.

The total concentration of polysaccharide present in the freshening composition may be less than about 0.5 wt. %, or preferably less than about 0.2 wt. %, or preferably less than about 0.1 wt. %, more preferably less than 0.08 wt. %, and most preferably less than 0.06 wt. %. Without wishing to be bound by theory, it is believed that minimizing the total polysaccharide level present in the freshening composition diminishes residue and/or optimizes spray characteristics.

The polysaccharide system may have a weight-average molecular weight in the range of about 10,000 Daltons to about 15,000,000 Daltons, preferably about 200,000 Daltons to about 10,000,000 Daltons, more preferably about 500,000 Daltons to about 9,000,000 Daltons, more preferably about 750,000 Daltons to about 8,000,000 Daltons, more preferably about 1,000,000 Daltons to about 7,000,000 Daltons, more preferably about 2,000,000 Daltons to about 6,000,000 Daltons, more preferably about 3,500,000 Daltons to about 6,000,000 Daltons.

The polysaccharide may be characterized by the ratio of acetylation. The ratio of acetylation of one or more of the polysaccharides, such as xanthan gum, may be in the range of about 5.0 to about 0.2, preferably in the range of about 3.5 to about 0.3, preferably in the range of about 2.0 to about 0.35, preferably in the range of about 1.5 to about 0.37, preferably in the range of about 1.0 to about 0.39.

The freshening composition may have a total protein level of less than about 100 parts per million (ppm), preferably less than 50 ppm, preferably less than 25 ppm, more preferably less than 10 ppm. It may be desirable to limit the total protein level in the freshening composition in order to minimize discoloring of surfaces to which the freshening composition is applied.

Buffering Agent

The freshening composition may include a buffering agent which may be a carboxylic acid, or a dicarboxylic acid like maleic acid, or a polybasic acid such as citric acid or polyacrylic acid. The acid may be sterically stable, and used in this freshening composition for maintaining the desired pH. The buffering agent may also comprise abase such as triethanolamine, or the salt of an organic acid such as sodium citrate. The freshening composition may have a pH from about 3.0 to about 7.0, preferably about 4.0 to about 6.5, more preferably about 4.0 to about 6.0.

Carboxylic acids such as citric acid may act as metal ion chelants and can form metallic salts with low water solubility. The freshening composition may be essentially free of citric acids. The buffer can be alkaline, acidic or neutral.

Other suitable buffering agents for freshening compositions include biological buffering agents. Some examples are nitrogen-containing materials, sulfonic acid buffers like 3-(N-morpholino)propanesulfonic acid (MOPS) or N-(2-Acetamido)-2-aminoethanesulfonic acid (ACES), which have a near neutral 6.2 to 7.5 pKa and provide adequate buffering capacity at a neutral pH. Other examples are amino acids such as lysine or lower alcohol amines like mono-, di-, and tri-ethanolamine. Other nitrogen-containing buffering agents are tri(hydroxymethyl)aminomethane (HOCH2)3CNH3 (TRIS), 2-amino-2-ethyl-1,3-propanediol, 2-amino-2-methyl-propanol, 2-amino-2-methyl-1,3-propanol, disodium glutamate, N-methyl diethanolamide, 2-dimethylamino-2-methylpropanol (DMAMP), 1,3-bis(methylamine)-cyclohexane, 1,3-diamino-propanol N,N'-tetra-methyl-1,3-diamino-2-propanol, N,N-bis(2-hydroxyethyl)glycine (bicine) and N-tris (hydroxymethyl)methyl glycine (tricine). Mixtures of any of the above are also acceptable.

The freshening compositions may contain at least about 0 wt. %, preferably at least about 0.001 wt. %, more preferably at least about 0.01 wt. %, by weight of the freshening composition, of a buffering agent. The freshening composition may also contain no more than about 1 wt. %, preferably no more than about 0.75 wt. %, more preferably no more than about 0.5 wt. %, by weight of the freshening composition, of a buffering agent.

Solubilizer

The freshening composition may contain a solubilizing aid to solubilize any excess hydrophobic organic materials, particularly some malodor counteractants, perfume materials, and also optional ingredients (e.g., insect repelling agent, antioxidant, etc.) which can be added to the freshening composition, that are not readily soluble in the freshening composition, to form a clear, translucent solution. A suitable solubilizing aid is a surfactant, such as a no-foaming or low-foaming surfactant. Suitable surfactants are nonionic surfactants, cationic surfactants, amphoteric surfactants, zwitterionic surfactants, and mixtures thereof.

The freshening composition may contain nonionic surfactants, cationic surfactants, and mixtures thereof. The freshening composition may contain ethoxylated hydrogenated castor oil. One type of suitable hydrogenated castor oil that may be used in the freshening composition is sold as Basophor™, available from BASF.

Freshening compositions containing anionic surfactants and/or detergent surfactants may make fabrics susceptible to soiling and/or leave unacceptable visible stains on fabrics as the solution evaporates off of the fabric. The freshening composition may be free of anionic surfactants and/or detergent surfactants.

The freshening composition may comprise from about 0.01 wt. % to about 3 wt. %, preferably from about 0.4 wt. % to about 1 wt. %, more preferably from about 0.1 wt. % to about 0.5 wt. %, most preferably from about 0.1 wt. % to about 0.3 wt. % of solublizing agent. Preferably the solubilizing agent is selected from the group consisting of a surfactant, a solvent and mixtures thereof. Preferably the surfactant comprises a non-ionic surfactant and preferably the solvent comprises an alcohol, a polyol and mixtures thereof.

Surface Tension Reducing Agent

The freshening composition may include a wetting agent that provides a low surface tension that permits the freshening composition to spread readily and more uniformly on hydrophobic surfaces like polyester and nylon. It has been found that the freshening composition, without such a wetting agent may not spread satisfactorily. The spreading of the freshening composition also allows it to dry faster, so that the treated material is ready to use sooner. Furthermore, a freshening composition containing a wetting agent may penetrate hydrophobic, oily soil better for improved malodor neutralization. A freshening composition containing a wetting agent may also provide improved "in-wear" electrostatic control. For concentrated freshening compositions, the wetting agent facilitates the dispersion of many actives such as antimicrobial actives and perfumes in the concentrated freshening compositions.

Nonlimiting examples of wetting agents include block copolymers of ethylene oxide and propylene oxide. Suitable block polyoxyethylene-polyoxypropylene polymeric surfactants include those based on ethylene glycol, propylene glycol, glycerol, trimethylolpropane and ethylenediamine as the initial reactive hydrogen compound. Polymeric compounds made from a sequential ethoxylation and propoxylation of initial compounds with a single reactive hydrogen atom, such as $C_{12-18}$ aliphatic alcohols, are not generally compatible with the cyclodextrin. Certain of the block polymer surfactant compounds include Pluronic® and Tetronic® by the BASF-Wyandotte Corp., Wyandotte, Mich.

Nonlimiting examples of wetting agents of this type are described in U.S. Pat. No. 5,714,137 and include the Silwet® surfactants available from Momentive Performance Chemical, Albany, N.Y. Exemplary Silwet surfactants are as follows:

| Name | Average MW |
|---|---|
| L-7608 | 600 |
| L-7607 | 1,000 |
| L-77 | 600 |
| L-7605 | 6,000 |
| L-7604 | 4,000 |
| L-7600 | 4,000 |
| L-7657 | 5,000 |
| L-7602 | 3,000; | and mixtures thereof.

The freshening composition may provide restoration of fabric such as its surface appearance (reduction of wrinkling, improved color appearance, improved or restored fabric shape). Adjunct ingredients that help restore fabric appearance are selected from: water-soluble or miscible quaternary ammonium surfactants and water-insoluble oil components together with surfactants, emulsifiers, and solvents needed to form a freshening composition that is stable and does not separate. Some nonlimiting preferred emulsifiers are sorbitan esters and sorbitan esters modified with alkylene oxides, such as Tween® 20 (polyoxyethylene (20)sorbitan monolaurate, branched surfactants, like Guerbet alcohols or alkylene oxide modified Guerget alcohols such as Lutensol® XL 70 (Oxirane, 2-methyl-, polymer with oxirane, mono(2-propylheptyl) ether, BASF). Wetting agents aid in spreading components and in reducing foaming of the freshening composition during spraying. Some preferred wetting agents include the class of wetting agents known in the art as superwetters. Not to be bound by theory, superwetters pack very efficiently at surfaces resulting in an extremely low equilibrium surface tension. Non-limiting examples of such surfactants include Surfynols® like Surfynol® 465 and Surfynol® 104PG 50 (Dow Chemicals).

Water-Soluble or Miscible Quaternary Ammonium Surfactant:

Typically, minimum levels of the water-soluble quat included in the freshening compositions are at least about 0.01 wt. %, preferably at least about 0.05 wt. %, more preferably at least about 0.1 wt. % even more preferably at least about 0.2 wt. %, based on the total weight of the freshening composition. Typically maximum levels of water-soluble quaternary agent included in the freshening composition are up to about 20 wt. %, preferably less than about 10 wt. %, and more preferably less than about 3 wt. % based on the total weight of the freshening composition. Typically, the agent is present in the freshening composition in an amount of about 0.2 wt. % to about 1.0 wt. %.

Specifically, the preferred water-soluble quaternary compounds are dialkyl quaternary surfactant compounds. Suitable quaternary surfactants include, but are not limited to, quaternary ammonium surfactants having the formula:

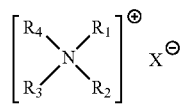

wherein $R_1$ and $R_2$ are individually selected from the group consisting of $C_1$-$C_4$ alkyl, $C_1$-$C_4$ hydroxy alkyl, benzyl, and —$(C_2H_4O)_xH$ where x has a value from about 2 to about 5; X is an anion; and (1) $R_3$ and $R_4$ are each a $C_6$-$C_{14}$ alkyl or (2) $R_3$ is a $C_6$-$C_{18}$ alkyl, and $R_4$ is selected from the group consisting of $C_1$-$C_{10}$ alkyl, $C_1$-$C_{10}$ hydroxy alkyl, benzyl, and —$(C_2H_4O)_xH$ where x has a value from 2 to 5. Preferred asymmetric quaternary compounds are compounds where R3 and R4 are not identical, and preferably one is branched and the other one is linear.

An example of a preferred asymmetric quaternary compound is ARQUAD HTL8-MS where X is a methyl sulfate ion, R1 and R2 are methyl groups, R3 is a hydrogenated tallow group with <5% mono unsaturation, and R4 is a 2-ethylhexyl group. ARQUAD HTL8-MS is available from Akzo Nobel Chemical of Arnhem, Netherlands.

An example of a suitable symmetric quaternary compound is UNIQUAT 22c50 where X is a carbonate and bicarbonate, R1 and R2 are methyl groups, R3 and R4 are C10 alkyl groups.

UNIQUAT 22c50 is a registered trademark of Lonza and in North America is available thru Lonza Incorporated of Allendale, N.J.

Another example of a suitable water-soluble quaternary compound is BARQUAT CME-35 which is N-Cetyl Ethyl Morpholinium Ethosulfate available from Lonza and having the following structure:

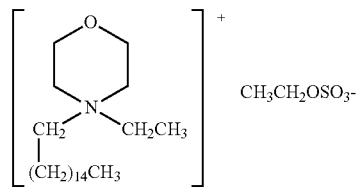

Antimicrobial Compounds

The freshening composition may include an effective amount of a compound for reducing the number of viable microbes in the air or on inanimate surfaces. Antimicrobial compounds are effective on gram negative or gram positive bacteria or fungi typically found on indoor surfaces that have contacted human skin or pets such as couches, pillows, pet bedding, and carpets. Such microbial species include *Klebsiella pneumoniae, Staphylococcus aureus, Aspergillus niger, Klebsiella pneumoniae, Streptococcus pyogenes, Salmonella choleraesuis, Escherichia coli Trichophyton mentagrophytes*, and *Pseudomonas aeruginosa*. The antimicrobial compounds may also be effective at reducing the number of viable viruses such H1-N1, Rhinovirus, Respiratory Syncytial, Poliovirus Type 1, Rotavirus, Influenza A, Herpes simplex types 1 & 2, Hepatitis A, and Human Coronavirus.

Antimicrobial compounds suitable in the freshening composition can be any organic material which will not cause damage to fabric appearance (e.g., discoloration, coloration such as yellowing, bleaching). Water-soluble antimicrobial compounds include organic sulfur compounds, halogenated compounds, cyclic organic nitrogen compounds, low molecular weight aldehydes, quaternary compounds, dehydroacetic acid, phenyl and phenoxy compounds, or mixtures thereof.

A quaternary compound may be used. Examples of commercially available quaternary compounds suitable for use in the freshening composition are Barquat available from Lonza Corporation; and didecyl dimethyl ammonium chloride quat under the trade name Bardac® 2250 from Lonza Corporation.

The antimicrobial compound may be present in an amount from about 500 ppm to about 7000 ppm, alternatively about 1000 ppm to about 5000 ppm, alternatively about 1000 ppm to about 3000 ppm, alternatively about 1400 ppm to about 2500 ppm, by weight of the freshening composition.

Preservatives

The freshening composition may include a preservative. The preservative may be present in an amount sufficient to prevent spoilage or prevent growth of inadvertently added microorganisms for a specific period of time, but not sufficient enough to contribute to the odor neutralizing performance of the freshening composition. In other words, the preservative is not being used as the antimicrobial compound to kill microorganisms on the surface onto which the freshening composition is deposited in order to eliminate odors produced by microorganisms. Instead, it is being used to prevent spoilage of the freshening composition in order to increase the shelf-life of the freshening composition.

The preservative can be any organic preservative material which will not cause damage to fabric appearance, e.g., discoloration, coloration, bleaching. Suitable water-soluble preservatives include organic sulfur compounds, halogenated compounds, cyclic organic nitrogen compounds, low molecular weight aldehydes, parabens, propane diaol materials, isothiazolinones, quaternary compounds, benzoates, low molecular weight alcohols, dehydroacetic acid, phenyl and phenoxy compounds, or mixtures thereof.

Non-limiting examples of commercially available water-soluble preservatives include a mixture of about 77% 5-chloro-2-methyl-4-isothiazolin-3-one and about 23% 2-methyl-4-isothiazolin-3-one, a broad spectrum preservative available as a 1.5% aqueous solution under the trade name Kathon® CG by Rohm and Haas Co.; 5-bromo-5-nitro-1,3-dioxane, available under the tradename Bronidox L® from Henkel; 2-bromo-2-nitropropane-1,3-diol, available under the trade name Bronopol® from Inolex; 1,1'-hexamethylene bis(5-(p-chlorophenyl)biguanide), commonly known as chlorhexidine, and its salts, e.g., with acetic and digluconic acids; a 95:5 mixture of 1,3-bis(hydroxymethyl)-5,5-dimethyl-2,4-imidazolidinedione and 3-butyl-2-iodopropynyl carbamate, available under the trade name Glydant Plus® from Lonza; N-[1,3-bis(hydroxymethyl)2,5-dioxo-4-imidazolidinyl]-N,N-bis(hydroxy-methyl) urea, commonly known as diazolidinyl urea, available under the trade name Germall® II from Sutton Laboratories, Inc.; N,N"-methylenebis{N'-[1-(hydroxymethyl)-2,5-dioxo-4-imidazolidinyl]urea}, commonly known as imidazolidinyl urea, available, e.g., under the trade name Abiol® from 3V-Sigma, Unicide U-13® from Induchem, Germall 115® from Sutton Laboratories, Inc.; polymethoxybicyclicoxazolidine, available under the trade name Nuosept® C from Hüls America; formaldehyde; glutaraldehyde; polyaminopropyl biguanide, available under the trade name Cosmocil CQ® from ICI Americas, Inc., or under the trade name Mikrokill® from Brooks, Inc; dehydroacetic acid; and benzsiothiazolinone available under the trade name Koralone™ B-119 from Rohm and Hass Corporation; 1,2-Benzisothiazolin-3-one; Acticide MBS.

Suitable levels of preservative are from about 0.0001 wt. % to about 0.5 wt. %, alternatively from about 0.0002 wt. % to about 0.2 wt. %, alternatively from about 0.0003 wt. % to about 0.1 wt. %, by weight of the freshening composition.

Malodor Counteractants

The freshening composition may include other malodor reducing technologies. This may include, without limitation, amine functional polymers, metal ions, cyclodextrins, cyclodextrin deriviatives, polyols, oxidizing agents, activated carbon, and combinations thereof.

Perfume Delivery Technologies

The freshening compositions may comprise one or more perfume delivery technologies that stabilize and enhance the deposition and release of perfume ingredients from treated substrate. Such perfume delivery technologies can also be used to increase the longevity of perfume release from the treated substrate. Perfume delivery technologies, methods of making certain perfume delivery technologies and the uses of such perfume delivery technologies are disclosed in US 2007/0275866 A1.

The freshening compositions may comprise from about 0.001 wt. % to about 20 wt. %, preferably from about 0.01 wt. % to about 10 wt. %, preferably from about 0.05 wt. % to about 5 wt. %, more preferably from about 0.1 wt. % to about 0.5 wt. % by weight of the perfume delivery technology. In one aspect, the perfume delivery technologies may be selected from the group consisting of: pro-perfumes, polymer particles, soluble silicone, polymer assisted delivery, molecule assisted delivery, fiber assisted delivery, amine assisted delivery, cyclodextrins, starch encapsulated accord, zeolite and inorganic carrier, and mixtures thereof.

The perfume delivery technology may comprise an amine reaction product (ARP) or a thio reaction product. One may also use "reactive" polymeric amines and or polymeric thiols in which the amine and/or thiol functionality is pre-reacted with one or more PRMs to form a reaction product Typically the reactive amines are primary and/or secondary amines, and may be part of a polymer or a monomer (non-polymer). Such ARPs may also be mixed with additional PRMs to provide benefits of polymer-assisted delivery and/or amine-assisted delivery. Nonlimiting examples of polymeric amines include polymers based on polyalkylimines, such as polyethyleneimine (PEI), or polyvinylamine (PVAm). Nonlimiting examples of monomeric (non-polymeric)amines include hydroxyl amines, such as 2-aminoethanol and its alkyl substituted derivatives, and aromatic amines such as anthranilates. The ARPs may be premixed with perfume or added separately in leave-on or rinse-off applications. A material that contains a heteroatom other than nitrogen and/or sulfur, for example oxygen, phosphorus or selenium, may be used as an alternative to amine compounds. The aforementioned alternative compounds can be used in combination with amine compounds. A single molecule may comprise an amine moiety and one or more of the alternative heteroatom moieties, for example, thiols, phosphines and selenols. The benefit may include improved delivery of perfume as well as controlled perfume release. Suitable ARPs as well as methods of making same can be found in USPA 2005/0003980 A1 and U.S. Pat. No. 6,413,920 B1.

Unencapsulated Perfume

The freshening composition may include unencapsulated perfume comprising one or more perfume raw materials that solely provide a hedonic benefit (i.e. that do not neutralize malodors yet provide a pleasant fragrance). Suitable perfumes are disclosed in U.S. Pat. No. 6,248,135. For example, the freshening composition may include a mixture of volatile aldehydes for neutralizing a malodor and hedonic perfume aldehydes.

Where perfumes, other than the volatile aldehydes in the malodor control component, are formulated into the freshening composition, the total amount of unencapsulated perfumes and volatile aldehydes may be from about 0.015 wt. % to about 3 wt. %, preferably from about 0.01 wt. % to about 1.0 wt. %, more preferably from about 0.015 wt. % to about 0.5 wt. %, by weight of the freshening composition.

Aqueous Carrier

The freshening composition may include an aqueous carrier. The aqueous carrier which is used may be distilled, deionized, or tap water. Water may be present in any amount for the freshening composition to be an aqueous solution. Water may be present in an amount of about 85 wt. % to 99.5 wt. %, preferably about 90 wt. % to about 99.5 wt. %, more preferably about 92 wt. % to about 99.5 wt. %, more preferably about 95 wt. %, by weight of the freshening composition. Water containing a small amount of low molecular weight monohydric alcohols, e.g., ethanol, methanol, and isopropanol, or polyols, such as ethylene glycol and propylene glycol, can also be useful. However, the volatile low molecular weight monohydric alcohols such as ethanol and/or isopropanol should be limited since these volatile organic compounds will contribute both to flammability problems and environmental pollution problems. If small amounts of low molecular weight monohydric alcohols are present in the freshening composition due to the addition of these alcohols to such things as perfumes and as stabilizers for some preservatives, the level of monohydric alcohol may about 1 wt. % to about 5 wt. %, alternatively less than about 6 wt. %, alternatively less than about 3 wt. %, alternatively less than about 1 wt. %, by weight of the freshening composition.

Diluents

The freshening composition may also include diluents. Exemplary diluents include dipropylene glycol methyl ether, and 3-methoxy-3-methyl-1-butanol, and mixtures thereof.

Adjuvants

Adjuvants can be added to the freshening composition herein for their known purposes. Such adjuvants include, but are not limited to, water soluble metallic salts, including zinc salts, copper salts, and mixtures thereof; antistatic agents;

insect and moth repelling agents; colorants; antioxidants; aromatherapy agents and mixtures thereof.

Sprayable Product

The freshening composition may be packaged in a spray dispenser to form a sprayable product. The sprayable product may be suitable for use in air and on surfaces.

The sprayable product may be configured to deliver a fine mist. The spray dispenser may be configured in various ways, such as a direct compression-type trigger sprayer, a pre-compression-type trigger sprayer, or an aerosol-type spray dispenser. One suitable spray dispenser is the TS800 Trigger Sprayer (Exxon Mobil PP1063, material classification 10003913, Manufacturer-Calmar).

Another suitable spray dispenser includes a continuous action sprayer, such as FLAIROSOL™ dispenser from Afa Dispensing Group. The FLAIROSOL™ dispenser includes a bag-in-bag or bag-in-can container with a pre-compression spray engine, and aerosol-like pressurization of the freshening composition.

The sprayable product may include a spray engine and a container. The freshening composition may be disposed in the container. The container comprising the freshening composition may be available separately from the spray engine, such a refill container.

Performance Characteristics

It has been found that the freshening compositions of the present disclosure are stable, exhibit a consumer-acceptable spray and have minimal residue. Not wishing to be bound by theory, it is believed that the structurant system of the present disclosure binds uniquely together in a highly effective manner to provide stability at very small polysaccharide concentrations and enable consumer-acceptable spray quality with minimal residue.

The freshening composition may be dispensed from a spray dispenser in the form of spray droplets. A freshening composition of the present disclosure is able to suspend particles, forming a stable freshening composition, while also delivering spray droplets of a relatively uniform and sufficiently small size. Larger and non-uniform spray droplets may deliver an unacceptable appearance to a consumer and may not provide sufficient coverage of the freshening composition in the air or on a surface.

The freshening compositions may also deliver a sufficiently low and consumer acceptable level of residue on a surface after the freshening composition is sprayed and dried onto a surface. For example, preferred freshening compositions of the present disclosure may provide a residue value in the range of 0 to less than 20 or preferably 0 to less than 15 measured according to the RESIDUE VALUE TEST METHOD.

A structurant system of the present disclosure may suspend the particles in the freshening composition such that the particles do not float to the top of the freshening composition or sink to the bottom of the freshening composition. For example, freshening compositions of the present disclosure may provide a phase stability grade measured according to the PHASE STABILITY TEST METHOD disclosed herein of at least 1 or 2. Stabilizing the particles in the freshening composition eliminates the need to shake the spray dispenser vigorously before dispensing the freshening composition. Stabilizing the particles may also help to more evenly distribute the particles throughout the freshening composition so that each spray out of the spray dispenser provides a relatively consistent level of particles.

Rheology Characteristics

The yield stress of the final freshening composition may be in the range of greater than 0 to about 1,000 mPa, preferably greater than 0 to about 500 mPa, preferably greater than 0 to about 300 mPa, preferably greater than 0 to about 100 mPa, more preferably greater than 0 to about 50 mPa, as measured according to the RHEOLOGY TEST METHOD disclosed herein.

The viscosity of the freshening composition may be in the range of about 1 mPa-s to about 20 mPa-s, preferably about 1 mPa-s to about 15 mPa-s, preferably about 1 mPa-s to about 10 mPa-s, more preferably about 1 mPa-s to about 5 mPa-s, as measured according to the RHEOLOGY TEST METHOD disclosed herein.

Methods of Use

The freshening composition of the present invention can be used by dispersing, e.g., by placing the aqueous solution into a dispensing means, such as a spray dispenser and spraying an effective amount into the air or onto the desired surface or article. An effective amount as defined herein means an amount sufficient to freshen the air or surface and/or neutralize malodor to the point that it is not discernible by the human sense of smell yet not so much as to saturate or create a pool of liquid on an article or surface and so that, when dry, there is no visual deposit readily discernible. Dispersing can be achieved by using a spray device.

The present disclosure encompasses the method of dispersing an effective amount of the freshening composition onto household surfaces for reducing malodor and/or freshening the household surfaces. The household surfaces are selected from the group consisting of countertops, cabinets, walls, floors, such as carpets or rugs, bathroom surfaces, garbage and/or recycling receptacles, appliances, and kitchen surfaces.

The present disclosure encompasses the method of dispersing a mist of an effective amount of the freshening composition onto fabric and/or fabric articles for reducing malodor and/or freshening the fabric and/or fabric articles. The fabric and/or fabric articles include, but are not limited to, clothes, curtains, drapes, upholstered furniture, carpeting, bed linens, bath linens, tablecloths, sleeping bags, tents, car interior, e.g., car carpet, fabric car seats, shower curtains, etc.

The present disclosure encompasses the method of dispersing a mist of an effective amount of the freshening composition onto and into shoes for reducing malodor impression and/or freshening wherein the shoes are not sprayed to saturation.

The present disclosure relates to the method of dispersing a mist of an effective amount of the freshening composition for into the air for freshening and/or to neutralize malodor.

The present disclosure relates to the method of dispersing a mist of an effective amount of the freshening composition onto cat litter, pet bedding and pet houses for freshening and/or to neutralize malodor.

The present disclosure relates to the method of dispersing a mist of an effective amount of the freshening composition onto household pets for freshening and/or to neutralize malodor.

Methods of Manufacturing

Due to the rheological properties of the freshening compositions (shear-thinning and high yield stress), it has been found that manufacturing on a large, commercial-scale is sensitive to various process conditions, including, order of addition, shear rate, time of mixing, aeration, and/or process equipment design. The commercial-scale method of manufacturing the freshening composition may produce greater than 100 Kg hr-1, more preferably greater than 1,000 Kg hr-1 and most preferably more than 10,000 Kg hr-1 of freshening composition. The method of manufacturing may include a continuous process or processes, a batch process or processes, or a combination of continuous and batch processing.

Order of Addition

It has been found that the order of addition of the components of the freshening composition can affect the long-term stability and/or residue values of the freshening composition, when making at commercial scales. In particular, it has been found that it is advantageous to add the majority of ion-forming water-soluble ingredients to the freshening composition before the polysaccharides are added. Ion-forming water-soluble ingredients may include buffers, malodor counteractants, preservatives, salts, and combinations thereof, for example. If the majority of the ion-forming water-soluble ingredients are added after the polysaccharides have been combined to form the structured aqueous composition, an unpredictable and time-decaying polymer structure can result, which may take weeks to reach its final viscosity. Adding the polysaccharide ingredients after the majority of the ion-forming water-soluble ingredients have been added results in a more time stable, predictable yield stress, and/or lower residue freshening composition.

Aqueous Premix

The aqueous premix may include ion-forming water-soluble ingredients, water, solubilizer, pH and buffering agents. With reference to FIG. 1 for illustrative purposes only, first the aqueous carrier is added to a mix tank 10 and then an impeller 12 is started at a moderate intensity. Once the mix tank becomes turbulent, at least 80 wt. % of the ion-forming water-soluble ingredients may be added one at a time to the top of the mix tank. After each ingredient is added, the ingredients may be mixed for at least one minute before the next ingredient of the aqueous premix is added. Mixing intensity should be selected so as to avoid aeration and foaming of the aqueous premix. The ingredients of the aqueous premix may be added one at a time in any order. Following the optional addition of malodor counteractants, such as hydroxypropyl beta-cyclodextrin, a pH trimming step is performed with a buffering agent.

The pH may be trimmed to a final value of about 4.0 to about 7.0, or about 4.0 to about 6.5, or about 4.0 to about 6.0. Once a stable pH reading is achieved, the formation of the aqueous premix is complete.

Exemplary, non-limiting and illustrative, aqueous premix composition is shown in Tables 1A and 1B below.

TABLE 1A

Exemplary Aqueous Premix

| Aqueous Premix | | |
| --- | --- | --- |
| Water | Aqueous Carrier | Q.S |
| Koralone | Preservative | 0.1% |
| Ethanol | Aqueous Carrier | 3% |
| Diethylene Glycol | Solubilizer | 0.1% |
| Hydroxypropyl Beta Cyclodextrin 40% solution | Malodor Counteractant | 2% |
| Citric Acid 50% solution | Ph Buffer | 0.1% |
| Final pH | | 4.5 |

TABLE 1B

Exemplary Aqueous Premix

| Aqueous Premix | | |
| --- | --- | --- |
| Water | Aqueous Carrier | Q.S |
| Koralone | Preservative | 0.1% |
| Ethanol | Aqueous Carrier | 2.5% |
| Diethylene Glycol | Solubilizer | 0.2% |
| Hydroxypropyl Beta Cyclodextrin 40% solution | Malodor Counteractant | 0.75% |
| Citric Acid 50% solution | Ph Buffer | 0.09% |
| Sodium Chloride 20% solution | Stabilizer | 0.1% |
| Final pH | | 5.0 |

Structured Aqueous Composition

Once the aqueous premix is formed, the ingredients of the structurant system can be added to the aqueous premix to form a structured aqueous composition.

The polysaccharides of the structurant system may be added to the aqueous premix in various forms. For example, the polysaccharides may be added as a powder or as a polysaccharide premix where the powder is mixed with water and optionally a preservative and allowed to rest for a period of at least two hours and up to 2 weeks. If added as a polysaccharide premix, each polysaccharide system may be prepared as a separate polysaccharide premix.

After the aqueous premix is formed, the polymer network is formed in the aqueous premix by adding the polysaccharides one at a time.

Once the first and second polysaccharides combine, they form an viscoelastic polymer network, giving the product a yield stress at a surprisingly low concentration of total polysaccharide. The ideal process outcome is to form a fully homogenous polymer network, at reliable yield stress, in spite of process and material variation (polysaccharide gums such as xanthan, konjac, locust bean, and tara gum are natural materials subject to variation).

The preferred polymer network forms when the polysaccharides are fully homogenized together, mixed at low local concentration, and at a low shear rate and time.

For example, any of the polysaccharides can be selected as the first polysaccharide to be added first to the aqueous premix to form a first polysaccharide premix. The first polysaccharide should be added slowly and at moderate mixing intensity that disperses the polysaccharide into the aqueous premix. Aeration of the aqueous premix may be minimized or prevented. The polysaccharide may be added to the top of the mix tank or at various other entry points. The aqueous premix and the first polysaccharide may be mixed until the first polysaccharide is thoroughly dispersed in the aqueous premix. However, the mixing time should be kept to a minimum in order to preserve the increasing yield stress of the aqueous premix.

With each polysaccharide that is added, the viscosity of the aqueous premix increases. As such, before the second polysaccharide is added to the aqueous premix, the mixing intensity may be increased to account for the increasing viscosity.

Next, a second poly saccharide may be slowly mixed into the aqueous premix. The aqueous premix and first and second polysaccharides may be mixed until the first and second polysaccharides are thoroughly dispersed to form a structured aqueous composition. However, the mixing time should be kept to a minimum in order to preserve the increasing yield stress of the aqueous premix. The mixing intensity may be increased as the second polysaccharide is added to account for the increasing viscosity and yield stress as the polymer network forms. The second polysaccharide addition is completed at a controlled rate. The structured aqueous composition may be a homogenous, clear liquid with light aeration.

The viscosity of the structured aqueous composition may be in the range of about 2 mPa-s to about 100 mPa-s, preferably about 2 mPa-s to about 75 mPa-s, preferably about 2 mPa-s to about 50 mPa-s, more preferably about 2 mPa-s to about 20 mPa-s. The yield stress of the structured aqueous composition may be in the range of greater than 0 to about 2,000 mPa, preferably greater than 0 to about 1,000 mPa, more preferably greater than 0 to about 500 mPa. A minimum viscosity and yield stress helps suspend the particles, however maintaining the viscosity at 100 mPa-s and below and the yield stress at 1,000 mPa or below will reduce the shear needed to incorporate the plurality of particles.

Forming the Freshening Composition

Once the structured aqueous composition has been formed, the plurality of particles can be dispersed into the structured aqueous composition to form the freshening composition. The plurality of particles may be blended into the structured aqueous composition as a particle premix. The particle premix may comprise a carrier fluid and a plurality of particles. The structured aqueous composition and the particle premix have substantially different viscosities. In order to uniformly disperse the plurality of particles throughout the structured aqueous composition, a high mixing intensity may be required. Due to the high mixing intensity, the time of mixing the plurality of particles into the structured aqueous composition should be monitored so as to minimize the shear imparted into the structured aqueous composition. Aeration and foaming of the structured aqueous composition may be minimized.

Instead of a particle premix, the particles by themselves may be added to the structured aqueous composition.

The mixing time utilized to disperse the particles in the structured aqueous composition may be reduced to less than 25 minutes, or preferably less than 20 minutes, more preferably less than 15 minutes.

For particle premixes such as slurries of benefit agent delivery particles, the particle premix may have aggregated regions of higher viscosity than the remaining premix. The aggregated regions of higher viscosity may have a size in the range of about 50 µm to about 400 µm. It may be beneficial to utilize a high mixing intensity in order to reduce the size of the aggregated regions to below 100 µm in the structured aqueous composition.

The viscosity of the freshening composition may be in the range of about 1 mPa-s to about 20 mPa-s, preferably about 1 mPa-s to about 15 mPa-s, preferably about 1 mPa-s to about 10 mPa-s, more preferably about 1 mPa-s to about 5 mPa-s. The yield stress of the freshening composition may be in the range of greater than 0 to about 1,000 mPa, preferably greater than 0 to about 500 mPa, preferably greater than 0 to about 300 mPa, preferably greater than 0 to about 100 mPa, more preferably greater than 0 to about 50 mPa. The shear applied to disperse the plurality of particles into the structured aqueous composition reduces the viscosity and yield stress. The lower viscosity and yield stress may enable the freshening composition to be sprayable, or in some cases an additional step may be required to further lower the viscosity and yield stress to a range that is sprayable from a spray dispenser.

Viscosity Trimming Step

The viscosity of the freshening composition may need to be reduced in order to make the freshening composition sprayable from a spray dispenser. A portion of ion-forming water-soluble ingredients may be used to reduce the viscosity of the freshening composition. This step may occur after the plurality of particles are dispersed throughout the structured aqueous composition to form the freshening composition. For example up to 500 mg/L or up to 200 mg/L of a mono or divalent salts may be added in order to adjust the final viscosity of the freshening composition.

The viscosity of the freshening composition may be in the range of about 1 mPa-s to about 20 mPa-s, preferably about 1 mPa-s to about 15 mPa-s, preferably about 1 mPa-s to about 10 mPa-s, more preferably about 1 mPa-s to about 5 mPa-s. The yield stress of the freshening composition may be in the range of greater than 0 to about 500 mPa, preferably greater than 0 to about 300 mPa, preferably greater than 0 to about 100 mPa, more preferably greater than 0 to about 50 mPa.

The freshening composition may have a residue value in the range of 0 to less than 20, preferably 0 to less than 15. The phase stability grade of the freshening composition may be 1 or 2, and more preferably the phase stability grade may be 2.

Process Equipment Design

Figure 2:
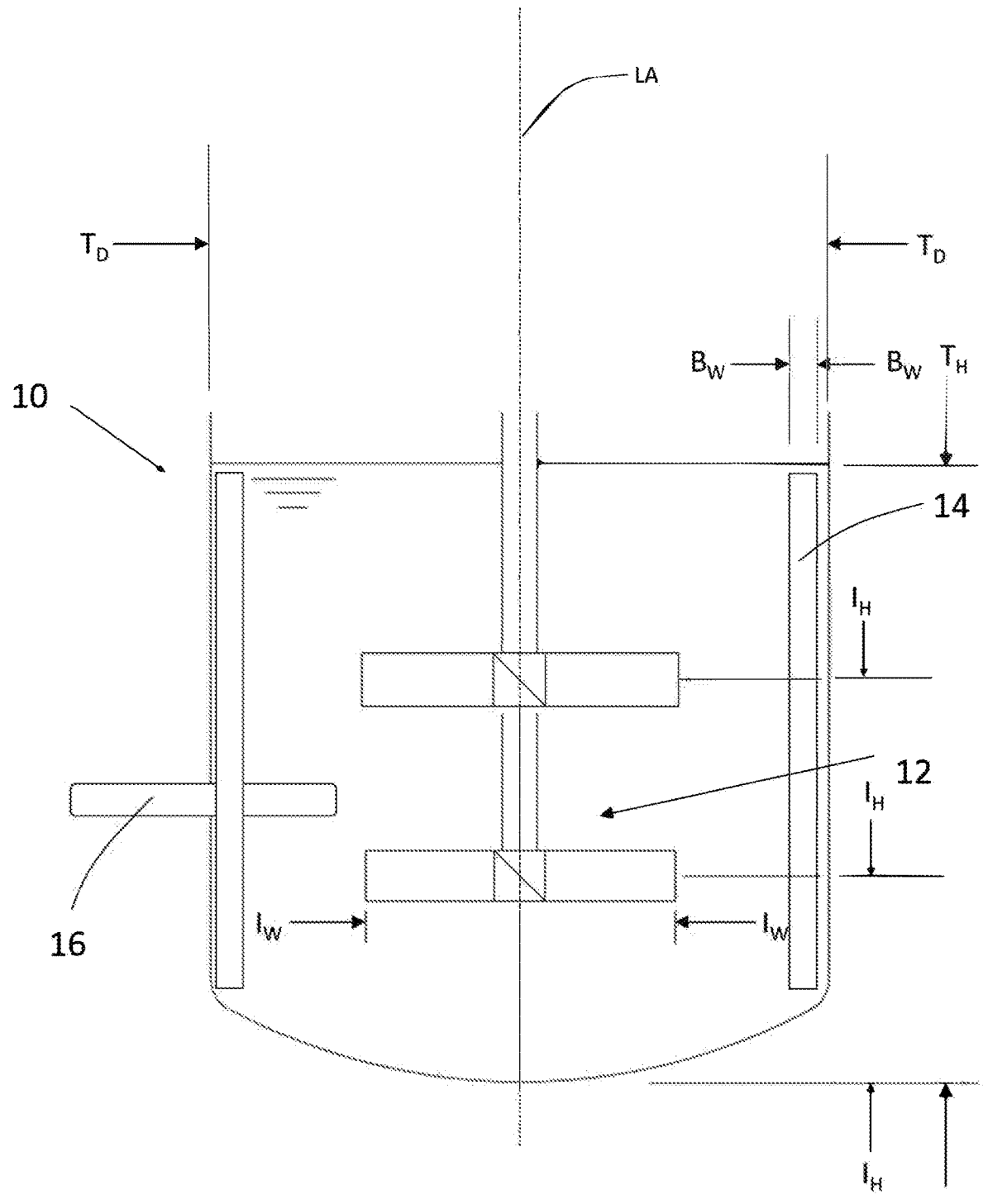
FIG. 2 is a sectional, schematic view of a mix tank of the present invention.

With reference to FIGS. 1 and 2, and as mentioned above, the freshening composition may be mixed in a mix tank 10. The mix tank 10 may be defined by a tank height $T_H$ and a tank diameter $T_D$. The tank height $T_H$ may be about 0.8 to about 2.0 times, or about 0.8 to about 1.4 times, the tank diameter $T_D$.

The mix tank 10 may include an impeller 12 that defines a longitudinal axis LA. The impeller 12 may comprise a plurality of blades. With reference to FIG. 2, at least two of the blades may be spaced from each other in the axial direction. The blades may define an impeller width $I_w$. The impeller width may be about 0.3 to about 0.6 times the tank diameter $T_D$, or the impeller width may be about 0.34 to about 0.5 times the tank diameter $T_D$. The impeller may be driven by a variable frequency drive ("VFD") motor in order to mix the freshening composition at a wide range of mixing intensities. Blades of the impeller may be positioned a distance from the bottom of the mix tank ("impeller height $I_H$") of about ⅓ of the tank diameter $T_D$. Where two or more blades of the impeller are axially spaced, lower blades may be positioned at an impeller height $I_H$ that is about ⅓ of the tank diameter $T_D$ and the upper blades may be positioned at an impeller height $I_H$ that is about ⅔ of the tank diameter $T_D$.

The impeller may be a PBT-type impeller that pumps downward. The impeller may pump downward at an angle of about 45 degrees. The blades of the impeller may be various shapes, including rectangular-shaped.

The mix tank 10 may comprise one or more baffles 14. The baffles 14 may be defined by a baffle width $B_w$. The mix tank 10 may include two baffles 14, or the mix tank may include 3 or more baffles 14. The baffle width $B_w$ may be about 0.05 to about 0.2 times the tank diameter $T_D$.

The mix tank 10 may include one or more side nozzles 16 for injecting ingredients of the freshening composition at specific locations in the mix tank 10. A side nozzle may be used for injecting the particles into the structured aqueous composition. The particles may enter the mix tank at relatively high velocity directly in the region of the impeller so that the impeller can help break apart the particle premix. The particles may enter the mix tank at a velocity of about 2 m/s to about 5 m/s directed at the downdraft of the impeller. Positive displacement pumps can be used to meter the particle premix at the desired rate.

The process may include a high shear rotor stator mixer located inside of the mix tank for mixing various ingredients of the freshening composition.

The process may include a static mixer in addition to or in replacement of the mix tank. If the process includes a static mixer and a mix tank, the static mixer may be located upstream or downstream of the mix tank for mixing various ingredients of the freshening compositions at various different stages of the process.

Test Methods

Rheology Test Method

To measure the yield stress and/or the viscosity of a sample, measurements are made with a TA Discovery HR-2 Hybrid Rheometer (TA Instruments, New Castle, Del., U.S.A.) and accompanying TRIOS software version 4.2.1.36612, or equivalent. The instrument is outfitted with a Concentric Cylinder Double Gap Cup (e.g., TA Instrument, cat. #546050.901), Double Gap Rotor (e.g. TA Instruments, cat. #546049.901) and Split Cover (e.g. TA Instruments, cat. #545626.001). The calibration is done in accordance with manufacturer recommendations. A refrigerated, circulating water bath set to 25° C. is attached to the Concentric Cylinder. The Concentric Cylinder temperature is set to 25° C. The temperature is monitored within the Control Panel until the instrument reaches the set temperature, then an additional 5 minutes is allowed to elapse to ensure equilibration before loading sample material into the Double Gap Cup.

The parameters for the Double Gap Cup are as follows: the inside cup diameter is 30.2 mm; the inside bob diameter is 32 mm; the outside bob diameter is 35 mm; the outside cup diameter is 37 mm; the inner cylinder height is 55 mm; the immersed height is 53 mm; the operating gap is 2,000.0 µm; the loading gap is 90,000.0 µm; the Environmental system is Peltier; and with a sample volume between 12 ml and 15 ml (preferably 12 ml).

To load the sample, a minimum of 12 ml of sample is added to the Double Gap Cup using a syringe, and the sample is then allowed to sit for 15 minutes, ensuring that any trapped air bubbles rise to the surface. The Double Gap Rotor is then lowered to the proper gap and data are collected in accordance with the following Settings and Procedures.

Data are collected in a series of steps conducted in precisely the following order: The Conditioning Sample Step is conducted using the following instrumental settings: Environmental Control is set with a Temperature of 25° C.; Inherit Set Point is selected as Off; Soak Time is set to 0.0 s; Wait for Temperature is selected as On; Wait for axial force is selected as Off; Preshear Options is set with a Perform Preshear selected as Off; Equilibrium is set with a Perform Equilibration selected as On; and Duration is set to 600.0 s.

The Flow Peak Hold Step is conducted using the following instrument settings: Environmental Control is set with a Temperature of 25° C.; Inherit Set Point is selected as Off; Soak Time is set to 0.0 s; Wait for Temperature is selected as Off; Test Parameters is set with a Duration of 600.0 s; Shear Rate is selected and set to 0.01 s-1; Inherit initial value is selected as Off; Sampling interval is selected and set to 3.0 s/pt; Controlled Rate Advanced is set with a Motor mode selected as Auto; Data acquisition is set with a End of step selected as Zero torque; Fast sampling is selected as Off; Save image is selected as Off; Step Termination is set with Limit checking Enabled selected as On; Terminate step when is set with Strain (%) selected, >selected, and set to 500%; Equilibrium Enabled is selected as Off; Step Repeat Enabled is selected as off.

The Conditioning Sample Step is conducted using the following instrumental settings: Environmental Control is set with a Temperature of 25° C.; Inherit Set Point is selected as Off; Soak Time is set to 10.0 s; Wait for Temperature is selected as Off; Wait for axial force is selected as Off; Preshear Options is set with a Perform Preshear selected as Off; Equilibrium is set with a Perform Equilibration selected as On; and Duration is set to 600.0 s.

The Flow Sweep Step is conducted using the following instrument settings: Environmental Control is set with a Temperature of 25° C.; Inherit Set Point is selected as Off; Soak Time is set to 0.0 s; Wait For Temperature is selected as Off; Test Parameters is set with Logarithmic sweep selected; Shear rate is selected and set to 1.0 e-3 s-1 to 1000.0 s-1; Points per decade is set to 5; Steady state sensing is selected as On; Max equilibration time is set to 45.0 s; Sample period is set to 5.0 s; % tolerance is set to 5.0; Consecutive within is set to 3; Scaled time average is selected as Off; Controlled Rate Advanced is set with Motor mode selected as Auto; Data acquisition is set with Save point display selected as Off; Save image is selected as Off; Step termination is set with Limit checking Enabled selected as Off; Equilibrium Enabled is selected as Off; Step Repeat Enabled is selected as Off.

The Conditioning End of Test Step is conducted using the following instrument settings: Set temperature is selected as Off; Set temperature system idle (only if axial force control is active) is selected as On.

The Yield Stress is calculated from the data collected in the Flow Peak Hold Step, in the following way: The data points are plotted as Stress (mPa) on the y-axis against Step Time (s) on the x-axis. The Yield Stress is determined by selecting the "Analysis" tab, then selecting "Signal max" from the Function drop down list and finally selecting "Analyze" in the Commands category. For a contiguous data set (containing a single stress value greater than zero for each time value), the Yield Stress equals the value of 'Max Y' if it occurs in the first 250 s and the Yield Stress equals zero if the value of 'Max Y' occurs after 250 s.

The Viscosity is determined to be the 'infinite rate viscosity' determined by selecting the 'Best Fit Flow (viscosity vs. rate)' for the viscosity curve in the analysis portion of the program, expressed in mPa s.

Phase Stability Test Method

Phase stability grades were determined by visual observation of the sample after one week of storage, in accordance with the following instructions. A 150 mL sample of product was placed in a clean 8 oz jar (eg VWR, CAT #16195-805, or equivalent) and seal tightly with a metal cap (eg VWR, CAT #89204-934, or equivalent), within one hour after preparation of the sample. The jar was placed in controlled temperature/controlled humidity room set to 25° C. and 60% Relative Humidity. The sealed sample jar was then left quiescent (e.g. no shaking or mixing) for one weeks.

After one weeks, the aged the product was visually assessed and graded for stability. To assess and grade the sample, the observer made every effort to determine whether there was any layer or heterogeneity of turbidity within the sample. This effort included using bright light and adjusting lighting direction as well as altering the direction of observations. A layer may be observed as an area that is more turbid (whiter). A layer may occur near the top surface of the product, and a layer may be very thin. Care was taken to ensure that the product was not be shaken or mixed in any way before or during observation and assessment process. Phase Stability was graded on the following Phase Stability Grading Scale:

A grade of 2 was given if the sample appeared stable as no layer or phase separation was observed and the sample was deemed to be of homogeneous turbidity throughout;

A grade of 1 was given if the sample appeared moderately stable as a possible phase separation layer was observed that was difficult to distinguish and turbidity in the sample was largely unchanged during the one week of storage;

A grade of 0 was given if the sample appeared Unstable as an obvious layer or separation within the sample was observed or a significant change in turbidity occurred during the one weeks of storage.

All newly created samples were placed into the storage room within one hour of their preparation and with minimal agitation. Samples for testing were obtained without spray dispensing the composition. Samples analyzed included 'Example Products' which were samples enabled by this invention and prepared in accordance with the details specified in the EXAMPLES section, herein.

Residue Value Test Method

The RESIDUE VALUE TEST METHOD measures white residue on black fabric swatches left from controlled spray of the test composition. All procedures and product are maintained at 25° C. (±5° C.) before and during the performance of the Test Method.

The black fabric swatch is composed of 70% Polyester and 30% Rayon (Black Amaretto, UPC 400068889522, SKU 6888952, Jo-Ann Stores, Inc., or equivalent) and cut into continuous rectangular dimensions of about 9.75×8.75 inches.

The black fabric swatch is mounted on the plexiglass stand (picture). The plexiglass stand is composed of piece of ¼ inch thick piece of plexiglass with square dimensions of about 21 inches. It is mounted to be 45 degrees relative to the bench. The plexiglass is cleaned with either ethanol-dampened paper towel or with a Santi-wipes. Once dried, the plexiglass is first covered with a paper towel and second with a black fabric swatch. They are fastened firmly in place with clothes pins on the left and right sides.

A test composition is sprayed and dried on the black fabric swatch. The test composition is placed in a bottle that is attachable with a sprayer (Silgan Dispensing, Richmond, Va.; Part: TS800, Standard Shroud, Fine mist Nozzle, Standard Trigger with 1.30 ml Output and 28-400 Closure). The bottle is primed by spraying seven full strokes (one full stroke defined as compressing the trigger from an uncompressed state to fully compressed) through the sprayer into a waste container. None of these composition from the priming sprays should land on the black fabric swatches. The bottle and sprayer are positioned relative to the black fabric swatch, such that: 1) the output of the nozzle is 8 inches from the intended spray spot on the black fabric swatch, 2) the bottle and sprayer combination is always kept upright and standing orthogonal to the bench, and 3) positioned, such that the spray will travel approximately parallel to the bench and at 135 degrees to the black fabric swatch, when leaving the sprayer. At this point the composition is applied in three full strokes—the first stroke dispenses product on the upper third of the black fabric swatch, the second stroke dispenses product on the middle third of the black fabric swatch and the third stroke dispenses product on the lower third of the black fabric swatch. Each stroke should reflect a stroke as typically applied by a consumer, of 95 sprays per minute. The total time for dispensing these three strokes should not exceed 60 seconds. Immediately after the third stroke, the fabric is placed horizontally on the bench, which is covered with aluminum foil, and left to completely dry for a minimum of four hours. If any of the three strokes is incomplete or inhomogeneous in the spray quality, the Method should be repeated with a new black fabric swatch.

The amount of residue is determined by measuring whiteness on the black fabric swatch with image analysis. One skilled in the art of image processing can achieve comparable results by acquiring and analyzing each image in the following way.

The treated black fabric swatch is placed on an EPSON Perfection V600 Photo Color Scanner (or equivalent), with the treated side facing the scanner bed. A grayscale calibration step wedge (DGK Color Tools DKC-Pro Color Calibration & White Balance Chart Set, MFR #DKC-PRO SET OF 2) is placed on the scanner bed adjacent to the black fabric swatch, so that it is in the same image scan but does not in any way occlude the black fabric swatch. Care is taken so that the black fabric swatch remains perfectly flat—free of wrinkles or folds in the fabric. Once placed, the top of the scanner is closed on the black fabric swatch and step wedge.

The SCANNED IMAGE of the black fabric swatch is captured using the EPSON Scan software v. 3.9.3.0 (in Professional Mode) using the exact same settings for each scan. The settings for the scans are the following. In the Original Section, the Document Type is selected to be 'Reflective', the Document Source is selected to be 'Document Table' and the Auto Exposure Type is selected to be 'Photo'. In the Destination Section, the Image type is selected to be '16-bit Grayscale', the Speed priority scanning is not selected, the Resolution is set to be '600 dpi', the Document Size is selected to be 'W 8.48, H 11.68 inches', the Target Size is selected to be 'Original', W is set as '8.48', H is set as '11.68', 'inches' is selected, the scale is selected to be '100%' and the Trimming is selected to be 'Off'. In the Adjustments Section, the UnSharp Mask is not selected, the Level is selected to be 'Medium', the Descreening is not selected, the Screening Ruling is selected as 'General', the Color Restoration is not selected, the Backlight Correction is not selected, the Level is selected to be 'Medium', Dust Removal is not selected, Level is selected to be 'Medium', DIGITAL ICE Technology is not selected, and Level is selected to be 'Standard'.

The Configuration button is then selected, opening a new window. In the Preview tab, Preview image rotation is not selected, Units is selected to be 'inches', Quality Preview is not selected, Densitometer Sampling Area is selected to be '1×1 pixel', Eyedropper Sampling Area is selected to be '1×1 pixel', Auto Photo Orientation is not selected, the Thumbnail Cropping Area has the slider all the way to the left over Small. In the Color tab Color Control is selected, Continuous Auto Exposure is not selected, Display Gamma is selected to be '2.2', the Auto Exposure Level is selected as 'High', the ICM is not selected, and the fields within that section are grayed out, and No Color Correction is not selected. In the Film Size tab, the Medium Format Film Size is selected to be '6×4.5'. In the Other tab, the Correct Document Skew is not selected, the Show Texture is not selected, Save Settings is selected, and Work Area is set as C drive. In the Preview screen, the entire area of the image is selected, and the SCANNED IMAGE is then captured and saved as a TIFF file.

The TIFF image file is analyzed by custom software, with the following steps.
1. Obtain a 16 bit, 600 dpi gray scale SCANNED IMAGE from a scanner with good contrast as described above. The image must contain a gray scale calibration step wedge so the intensity can be standardized from one image to the next, in case the scanner brightness changes.
2. Next, a STANDARDIZED IMAGE requires standardizing the intensity of all pixels in the SCANNED IMAGE of the black fabric swatch using the step wedge for calibration. To standardize the intensity of each pixel, measure the average intensity (gray level) for each of the six steps in the step wedge of the SCANNED IMAGE. These measured values are represented as X1, X2, X3, X4, X5 and X6 from darker to lighter respectively. The desired (standardized) intensity values for each of the calibration steps are Y1=6175, Y2=14220, Y3=20062, Y4=27550, Y5=35369 and Y6=58710 from darker to lighter respectively. This creates six points: (X1,Y1), (X2,Y2), (X3,Y3), (X4,Y4), (X5,Y5) and (X6,Y6) use to determine fitting constants A, B and C determined by fitting the equation $y=A*(x*x)+B*(x)+C$.
3. Next, the STANDARDIZED IMAGE is created from the SCANNED IMAGE applying the equation in Step 2 to the gray level (X) of every pixel of the SCANNED IMAGE, to arrive at a standardized intensity (Y) image.
4. Next, a THRESHOLDED IMAGE is created by thresholding and filtering the STANDARDIZED IMAGE. First, the STANDARDIZED IMAGE is treated with a median filter with a window width of 17 by 17 pixels to reduce noise due to the weave of the fabric. Second, a threshold filter is applied using a triangle threshold to create a binary image where pixels with gray level above the threshold are selected (white) and background pixels below the threshold are not selected (black). The threshold technique is outlined by Zack et al. (Zack G. W., Rogers W. E. and Latt S. A. (1977), *Automatic Measurement of Sister Chromatid Exchange Frequency*" J. Histochem. Cytochem. 1977, 25 (7): 741-53). As described in the reference, a line is constructed between the maximum of the histogram at (b) and the lowest (or highest depending on context) value (a) in the histogram. The distance L normal to the line and between the line and the histogram h[b] is computed for all values from a to b. The level where the distance between the histogram and the line is maximal is the threshold level. Third, interior noise (small black holes in white blobs) is removed by filling in (making white) small black holes (less than 15 pixels in the 4-connected regions). Next white exterior noise (white blobs on the black background) are removed by considering small regions less than 1121 pixels (2 square mm) as noise. These are removed (made black), leaving only residue regions of 2 square mm or larger. The THRESHOLDED IMAGE is the final black-and-white binary image obtained after this 3-step noise removal process.

Finally, measurements are calculated from the white regions in the THRESHOLDED IMAGE. The area of interest is assumed to be the fabric-only portion of the image and does not include the intensity calibration chart or other non-fabric areas. We start by assuming that the bright (white) regions in the area of interest are undesirable residue, and the black regions are assumed to be fabric with no visible residue. The number of BLOBS equals total number of contiguous bright (white) regions. The AREA OF RESIDUE (white) is total white area, expressed in square millimeters. The reported RESIDUAL VALUE=AREA OF RESIDUE/BLOBS, in units of square millimeters.

EXAMPLES

TABLE 2

Freshening Composition Ingredients

| | Ingredient | Manufacturer | Lot Number |
|---|---|---|---|
| 1 | Deionized Water | Not Applicable | N/A |
| 2 | Koralone B-119 | Rohm & Haas | YY00I5H901 |
| 3 | Ethanol | EQUISTAR CHEMICALS L P | 1B000113727 |
| 4 | Diethylene Glycol | OLD WORLD INDUSTRIES INC | NATX231318 |
| 5 | Hydroxypropyl Beta CD | WACKER CEHMICAL CORP | 74LE364 |
| 6 | Citric Acid | Univar | CB039865003 |
| 7 | Konjac gum- Newstar 1420 | Newstar Chemical | Y20200102-2 |
| 8 | Xanthan gum CP Kelco, Keltrol CC | CPKelco | 8L559K |
| 9 | Voyager Zen PAC PC | Encapsys | 201914205 |
| 10 | Silwet L-700 | MPM | 16JSVW137 |
| 11 | Sodium Chloride | Morton | RT18130007 |

Example A

Example A is an inventive example that demonstrates the preparation of a fabric treatment composition, by an order of addition in which the structurant system is added after addition of the ion-forming water-soluble ingredients. By forming the polymer network after ion-forming water-soluble ingredients have been added to the water, the network is relatively weaker in yield stress and a lower viscosity than it would be in a pure water solution. This aids in dispersion of the high viscosity liquid benefit agent to suitable particle size, resulting in a low residue score on fabric. The polymer network strength provides stability to the particles over time.

In the present example, polysaccharides were first dispersed into stock solutions prior to inclusion in the product. Next, an aqueous premix containing the water and majority of the ion-forming water soluble ingredients were prepared in the 7 L mix tank. The structurant system was then added carefully to the aqueous premix, under a prescribed mixing intensity and time. After network formation, the particle premix is dispersed to minimize aggregated regions of the particle premix in the structured aqueous composition at high shear rate. A non-aqueous wetting agent (Silwet) was added in the final step at lower mixing intensity. The total batch time was 28 minutes.

Preparation of 1 wt % Xanthan Gum Stock Solution 500 grams of a xanthan gum solution was prepared using a Ross high shear mixer with fine screen rotor stator attachment, Model LCI-100T SN 109209, from Charles Ross & Son Company of Hauppague N.Y. 494.61 grams of water were added to a clean mix tank (1-liter glass beaker, VWR). 0.39 grams Koralone B-119 were added to the beaker, and stirred until homogeneously mixed. 5.0 grams xanthan gum were added quickly into the beaker while mixing at 5000 RPM using the Ross high shear mixer fitted with mixing blade (4 Blade Stainless Steel, 2.5" diameter). The stir rate was increased to 8000 RPM as the solution thickens, with continued mixing at 8000 rpm for an additional 300 seconds.

Preparation of 1 wt % Konjac Gum Stock Solution 500 grams of a konjac gum solution was prepared using the Ross high shear mixer. 494.61 grams of water were added to a clean mix tank (1-liter glass beaker, VWR). 0.39 grams Koralone B-119 were added to the vessel, and stirred until homogeneously mixed. Add 5.0 grams konjac gum were added quickly into the vessel while mixing at 5000 RPM using the Ross Mill Mixer fitted with mixing blade (4 Blade Stainless Steel, 2.5" diameter). The stir rate was increased to 8000 RPM as the solution thickens, with continued mixing at 8000 RPM for an additional 300 seconds.

Preparation of Aqueous Premix

The mix tank illustrated in FIG. 1 was used to prepare the aqueous premix, and subsequently mix the polysaccharide structure system into the aqueous premix. For each step in the aqueous premix making, the amount of material, mixing time, and mixing intensity as measured by impeller RPM is listed in Table 3. A small 50 g sample was taken for measurement of the parameters in Table 3.

For this Example A, the mix tank of FIG. 1 was defined by a total volume of 7 liters, a tank diameter $T_D$ of 10 inches, a tank height $T_H$ equal to the tank diameter $T_D$, an impeller width $I_w$ of 0.45 times the tank diameter $T_D$, and a baffle width $B_w$ of 0.0625 times the tank diameter $T_D$, and the height of the impeller $I_H$ may be 0.333 times the tank diameter $T_D$.

Preparation of First Polysaccharides Premix

Konjac gum stock solution, the first polysaccharide of the structurant system in this example, was added to the aqueous premix in the mix tank. The amount of material, mixing time, and mixing intensity as measured by impeller RPM is listed in Table 4. A small 50 g sample was taken for measurement of the parameters in Table 4.

Preparation of the Structured Aqueous Composition

Xanthan gum stock solution, the second polysaccharide of the structurant system in this example, was then added to the first polysaccharide premix in the mix tank to form the structured aqueous composition. The amount of material, mixing time, and mixing intensity as measured by impeller RPM is listed in Table 5. A small 50 g sample was taken for measurement of the parameters in Table 5.

Preparation of the Freshening Composition

Voyager PAC PMC benefit agent and Silwet L7600 were added to the structured aqueous composition to form the freshening composition. The amount of material, mixing time, and mixing intensity as measured by impeller RPM is listed in Table 6. A small 50 g sample was taken for measurement of the parameters in Table 6.

Parameter Measurements

The compositions in Tables 3-6 were tested in accordance with the following methods:

The viscosity was determined by the RHEOLOGY TEST METHOD

The yield stress was determined by the RHEOLOGY TEST METHOD

The residue value was determined by the RESIDUE VALUE TEST METHOD

The phase stability grade was determined by the PHASE STABILITY TEST METHOD

TABLE 3

Example A Aqueous Premix

| Ingredient | Mass added | Impeller RPM during mixing step | Mixing Time |
|---|---|---|---|
| Water | 6296.5 g | 240 | 1 min |
| Koralone B-119 | 5.50 g | 240 | 1 min |
| Ethanol | 228.75 g | 240 | 1 min |
| Diethylene Glycol | 6.99 g | 240 | 2 min |
| Hydroxypropyl Beta CD | 52.65 g | 240 | 2 min |
| Citric Acid | 3.38 g | 240 | 7 min |
| Neat pH | | 4.5 | |
| Viscosity | | 1.8 mPa-s | |

TABLE 4

Example A First Polysachharide Premix

| Ingredient | Mass added | Impeller RPM during mixing step | Mixing Time |
|---|---|---|---|
| Aqueous Premix (Table 3) | Sum of Table 3 | 240 | 1 min |
| Konjac Gum stock solution | 205.16 g | 375 | 3 min |
| Viscosity | | 1.9 mPa-s | |
| Yield Stress | | 0 | |

TABLE 5

Example A Structured Aqueous Composition

| Ingredient | Mass added | Impeller RPM during mixing step | Mixing Time |
|---|---|---|---|
| First Polysaccharide Premix (Table 4) | Sum of Table 4 | 375 | 1 min |
| Xanthan Gum stock solution | 133.9 g | 425 | 3 min |
| Viscosity | | 3.5 mPa-s | |
| Yield Stress | | 282 mPa | |

TABLE 6

Freshening Composition

| Ingredient | Mass added | Impeller RPM during mixing step | Mixing Time |
|---|---|---|---|
| Structured Aqueous Composition (Table 5) | Sum of Table 5 | 425 | 1 min |
| Voyager PAC PMC | 66.7 g | 460 | 3 min |
| Silwet L7600 | 6.73 | 375 | 2 min |
| Viscosity | | 3.7 mPa-s | |
| Yield Stress | | 251 mPa | |
| Residue Score | | 70 | |
| Residue Score after 3 Days of Product age | | 12 | |
| Stability Grade | | Grade 1 | |

Example B

Example B provides a comparative example that demonstrates the preparation of a fabric treatment composition, by an order of addition in which the polysachharide polymer network is formed prior to the introduction of ion-forming water-soluble ingredients. By forming the network in a pure aqueous carrier solution, it becomes extremely strong, resulting in high yield stress, and viscosity. While this is good for stability, the highly non-Newtonian fluid is difficult to process at larger scales. Dispersing the particles below an acceptable size becomes challenging, resulting in high fabric residue scores.

In this example, the structurant system was first dispersed into stock solutions prior to addition of the ion-forming water-soluble ingredients. Next, the aqueous carrier, in this case water, was added to the 7 L mix tank such as illustrated in FIG. 1. The polysaccharide structure was then added carefully to the water, under a prescribed mixing intensity and time. After network formation, the benefit particles were dispersed to a small particle size in the structure at high shear rate. Next, the majority of the ion-forming water-soluble ingredients were added to the suspended particle composition at low energy. The total batch time was 25 minutes.

Preparation of 1 wt % Xanthan Gum Stock Solution 500 grams of a Xanthan gum solution was prepared using the Ross high shear mixer. 494.61 grams of water were added to a clean mix tank (1-liter glass beaker, VWR). 0.39 grams of Koralone B-119 were added to the beaker and stirred until homogeneously mixed. 5.0 grams of xanthan gum were added quickly into the beaker while mixing at 5000 RPM using the Ross Mill mixer fitted with mixing blade (4 blade stainless steel, 2.5" diameter). The stir rate was increased to 8000 RPM as the solution thickens, with continued mixing at 8000 rpm for an additional 300 seconds.

Preparation of 1 wt % Konjac Gum Stock Solution 500 grams of a xanthan gum solution was prepared using the Ross high shear mixer. 494.61 grams of water were added to a clean mix tank (1-liter glass beaker, VWR). 0.39 grams of Koralone B-119 were added to the vessel, and stirred until homogeneously mixed. Add 5.0 grams of konjac gum were added quickly into the vessel while mixing at 5000 RPM using the Ross Mill Mixer fitted with mixing blade (4 blade stainless steel, 2.5" diameter). The stir rate was increased to 8000 RPM as the solution thickens, with continued mixing at 8000 RPM for an additional 300 seconds.

Preparation of First Polysachharide Premix

Water and konjac gum stock solution were added to the mix tank. The amount of material, mixing time, and mixing intensity as measured by impeller RPM is listed in Table 7. A small 50 g sample was taken for measurement of the parameters in Table 7.

Preparation of Structured Aqueous Composition

Xanthan Gum Stock solution was added to the first polysaccharide premix in the mix tank. The amount of material, mixing time, and mixing intensity as measured by impeller RPM is listed in Table 8. A small 50 g sample was taken for measurement of the parameters in Table 8.

Preparation of Freshening Composition

Voyager PAC PMC benefit agent was added to the Structured Aqueous Composition. The amount of material, mixing time, and mixing intensity as measured by impeller RPM is listed in Table 9. A small 50 g sample was taken for measurement of the parameters in Table 9.

Preparation of the Freshening Composition Diluted with Ion-Forming Water-Soluble Ingredients The water-soluble ingredients listed in Table 4 were added to the suspended particle composition, diluting the mixture to the finished preparation. For each step in the dilution, the amount of material, mixing time, and mixing intensity as measured by impeller RPM is listed in table 10. A small 50 g sample was taken for measurement of the parameters in Table 10.

Parameter Measurements

The compositions in Tables 1-3 were tested in accordance with the following methods:

The viscosity was determined by the RHEOLOGY TEST METHOD

The yield stress was determined by the RHEOLOGY TEST METHOD

The residue value was determined by the RESIDUE VALUE TEST METHOD

The phase stability grade was determined by the PHASE STABILITY TEST METHOD

TABLE 7

Example B First Polysaccharide Premix

| Ingredient | Mass added | ImpellerRPM during mixing step | Mixing Time |
|---|---|---|---|
| Water | 6300 g | 240 | 1 min |
| Konjac Gum stock solution | 210.1 g | 375 | 3 min |
| Viscosity | 1.5 mPa-s | | |
| Yield Stress | 0 | | |

TABLE 8

Example B Structured Aqueous Composition

| Ingredient | Mass added | Impeller RPM during mixing step | Mixing Time |
|---|---|---|---|
| First Polysachharide Cmposition (Table 7) | Sum of Table 7 | 375 | 1 min |
| Xanthan Gum stock solution | 138 g | 425 | 3 min |
| Viscosity | 18.4 mPa-s | | |
| Yield Stress | 2573 mPa | | |

TABLE 9

Example B Addition of Suspended Particles to the Structured Aqueous Composition

| Ingredient | Mass added | Impeller RPM during mixing step | Mixing Time |
|---|---|---|---|
| Structured Aqueous Composition (Table 8) | Sum of Table 8 | 425 | 1 min |
| Voyager PAC PMC | 68.2 g | 450 | 3 min |
| Viscosity | 18.2 mPa-s | | |
| Yield Stress | 2103 mPa | | |

TABLE 10

Example B Freshening Composition Diluted with Aqueous Salts

| Ingredient | Mass added | Impeller RPM during mixing step | Mixing Time |
|---|---|---|---|
| Suspended particle composition (Table 3) | Sum of table 3 | 450 | 1 min |
| Diethylene Glycol | 6.54 g | 240 | 1 min |
| Silwet L-7600 | 6.59 g | 375 | 1 min |
| Hydroxypropyl Beta CD | 49.35 g | 240 | 1 min |
| Ethanol | 212.56 g | 240 | 1 min |
| Koralone B-119 | 5.14 g | 240 | 1 min |
| Citric Acid | 3.39 g | 240 | 7 min |
| Neat pH | 4.51 | | |
| Viscosity | 6.3 mPa-s | | |
| Yield Stress | 143 mPa | | |

TABLE 10-continued

Example B Freshening Composition Diluted with Aqueous Salts

| Ingredient | Mass added | Impeller RPM during mixing step | Mixing Time |
|---|---|---|---|
| Residue Score | 109 | | |
| Residue Score after Product rest for 3 days | 30 | | |
| Stability | Grade 1 | | |

TABLE 11

Summary Comparison of Example A and B

| All Parameters Measured for finished composition at Time noted | Example A | Example B |
|---|---|---|
| Viscosity 1 hour after making | 3.7 mPa-s | 6.3 mPa-s |
| Yield Stress 1 hour after making | 251 mPa | 143 mPa |
| Residue Score 72 hours after product making | 12 | 30 |
| Stability 1 month after making | Grade 1 | Grade 1 |

The consumer preferred product properties are those which result in a stable product (aided by high yield stress values), at low fabric residue, with a fine even spray on the fabric (aided by low viscosity). As shown in Table 11, the product in Example A shows preferred properties in all metrics.

Example C

Example C is an inventive example that demonstrates the preparation of a fabric treatment composition, by adding the polysachharide gums directly to the final batch, in which the polysachharide network is formed after aqueous ionic content addition.

First, water is added to a 7 L mix tank such as illustrated in FIG. 1. Next, an aqueous premix containing the water and majority of the aqueous salts is prepared in the mix tank. The polysaccharide structure is then added carefully to the aqueous premix, under a prescribed mixing intensity and time utilizing a High Shear IKA T25 Rotor stator mill (IKA Works T25 Digital Ultra Turrax with N 25 S Disperser Head, IKA Works, Inc, Wilmington, N.C. 28405, USA) to incorporate the powder. After network formation, the benefit particles are dispersed to a small particle size in the structure at high shear rate. A non-aqueous wetting agent (Silwet) is added in the final step at lower mixing intensity. The total batch time is 29 minutes.

For this Example C, the mix tank may have a total volume of 7 liters, a tank diameter $T_D$ of 10 inches, a tank height $T_H$ equal to the tank diameter $T_D$, an impeller width L, of 0.45 times the tank diameter $T_D$, and a baffle width B, of 0.0625 times the tank diameter $T_D$, and the height of the impeller $I_H$ may be 0.333 times the tank diameter $T_D$.

Preparation of Aqueous Premix

The mix tank described in FIG. 1 is used to prepare the aqueous premix, and subsequently mix the polysaccharide structure into the aqueous premix. For each step in the aqueous premix making the amount of material, mixing time, and mixing intensity as measured by impeller RPM is listed in Table 12.

Preparation of the First Polysaccharide Premix

Konjac gum powder is added to the aqueous premix in the mix tank. The amount of material, mixing time, and mixing intensity as measured by impeller RPM and Rotor Stator Mill operation RPM is listed in Table 13.

Preparation of Structured Aqueous Composition

Xanthan gum powder is added to first polysaccharide premix in the mix tank. The amount of material, mixing time, and mixing intensity as measured by impeller RPM is listed in Table 14.

Preparation of the Freshening Composition

Voyager PAC PMC Benefit agent and Silwet L7600 are added to the structured aqueous composition. The amount of material, mixing time, and mixing intensity as measured by impeller RPM is listed in Table 15.

TABLE 12

Example C Aqueous Premix

| Ingredient | Mass added | Impeller RPM during mixing step | Mixing Time |
|---|---|---|---|
| Water | 6493 g | 240 | 1 min |
| Koralone B-119 | 5.50 g | 240 | 1 min |
| Ethanol | 228.75 g | 240 | 1 min |
| Diethylene Glycol | 6.99 g | 240 | 2 min |
| Hydroxypropyl Beta CD | 52.65 g | 240 | 2 min |
| Citric Acid | 3.38 g | 240 | 7 min |

TABLE 13

Example C First Polysachharide Premix

| Ingredient | Mass added | Impeller RPM during mixing step | Mixing Time | IKA Mill RPM During Step |
|---|---|---|---|---|
| Aqueous Premix (Table 12) | Sum of Table 12 | 240 | 1 min | 0 |
| Konjac Gum stock solution | 2.06 g | 375 | 1 min | 7,500 |

TABLE 14

Example C Structured Aqueous Composition

| Ingredient | Mass added | Impeller RPM during mixing step | Mixing Time | IKA Mill RPM During Step |
|---|---|---|---|---|
| First Polysachharide Composition (Table 13) | Sum of Table 13 | 375 | 1 min | 7500 |
| Xanthan Gum stock solution | 133.9 g | 425 | 1 min | 7500 |

TABLE 15

Example C Freshening Composition

| Ingredient | Mass added | Impeller RPM during mixing step | Mixing Time | IKA Mill RPM During Step |
|---|---|---|---|---|
| Structured Aqueous Composition (Table 14) | Sum of Table 14 | 425 | 1 min | 7500 |
| Voyager PAC PMC | 66.7 g | 460 | 3 min | 0 |
| Silwet L7600 | 6.73 | 375 | 7 min | 0 |

Example D

Example D is an inventive example that demonstrates the preparation of a fabric treatment composition, by an order of addition in which the polysaccharide network is formed after addition of the aqueous ionic content.

Polysaccharides are first dispersed into stock solutions prior to inclusion in the product. Next, an aqueous premix containing the water and majority of the aqueous salts is prepared in the 100 L mix tank, such as illustrated in FIG. 2. The polysaccharide structure is then added carefully to the aqueous premix, under a prescribed mixing intensity and time. After network formation, the benefit particles are dispersed to a small particle size in the structure at high shear rate. A non-aqueous wetting agent (Silwet) is added in the final step at lower mixing intensity. The total batch Time is 47 minutes.

For the purpose of the following examples, the mix tank of FIG. 2 may be defined by a total volume of 100 liters, a tank diameter $T_D$ of 18 inches, a tank height $T_H$ that is 1.1 times the tank diameter $T_D$, an impeller width $I_w$ of 0.40 times the tank diameter $T_D$, and a baffle width $B_w$ of 0.0625 times the tank diameter $T_D$, and the height of the lower impeller $I_H$ may be ⅓ of the tank diameter $T_D$ and the height of the upper impeller $I_H$ may be ⅔ of the tank diameter $T_D$.

Preparation of 1 wt % Xanthan Gum Stock Solution 5000 grams of a xanthan gum solution is prepared using the Ytron Y0 High shear mixer (Ytron Y-0 Mixer, Quadro Engineering Corp of Waterloo, Canada, 0.25 HP, 50 mm Impeller diameter). 4946.1 grams of water are added to a clean mix tank (10 L glass beaker) 3.9 grams of Koralone B-119 are added to the beaker, and stirred until homogeneously mixed. 50 grams of xanthan gum are added quickly through a funnel and bypass tube to introduce the xanthan gum in the region of the impeller of the Ytron Y0 high shear mixer while mixing at 4900 RPM. Mixing at High shear is continued for 45 seconds until the powder is completely dispersed.

Preparation of 1 wt % Konjac Gum Stock Solution 5000 grams of a konjac gum solution is prepared using the Ytron Y0 high shear mixer. 4946.1 grams of water is added to a clean mix tank (10 L glass beaker). 3.9 grams of Koralone B-119 are added to the beaker and stirred until homogeneously mixed. 50 grams of konjac gum are added quickly through the funnel and bypass tube while mixing at 4900 RPM. Mixing at High shear is continued for 45 seconds until the powder was completely dispersed.

Preparation of Aqueous Premix

The mix tank described in FIG. 2 is used to prepare the aqueous premix, and subsequently mix the polysaccharide structure into the aqueous premix. For each step in the aqueous premix making the amount of material, mixing time, and mixing intensity as measured by impeller RPM is listed in Table 16.

Preparation of the First Polysaccharide Premix

Konjac gum stock solution was added to the aqueous premix in the mix tank. The amount of material, mixing time, and mixing intensity as measured by impeller RPM is listed in Table 17.

Preparation of the Structured Aqueous Composition

Xanthan gum stock solution is added to the first polysaccharide premix in the mix tank. The amount of material, mixing time, and mixing intensity as measured by impeller RPM is listed in Table 18.

Preparation of the Freshening Composition

Voyager PAC PMC benefit agent and Silwet L7600 are added to the structured aqueous composition. The amount of material, mixing time, and mixing intensity as measured by impeller RPM is listed in Table 19. A Sample is taken for pH Measurement

TABLE 16

Example D Aqueous Premix

| Ingredient | Mass added (g) | Impeller RPM during mixing step | Mixing Time |
|---|---|---|---|
| Water | 87928.3 | 188 | 1 min |
| Koralone B-119 | 78.125 | 188 | 1 min |
| Ethanol | 3457.22 | 188 | 2 min |
| Diethylene Glycol | 900.901 | 188 | 1 min |
| Hydroxypropyl Beta CD | 1580.53 | 188 | 2 min |
| Citric Acid | 29.4118 | 188 | 7 min |

TABLE 17

Example D First Polysaccharide Premix

| Ingredient | Mass added | Impeller RPM during mixing step | Mixing Time |
|---|---|---|---|
| Aqueous Premix (Table 16) | Sum of Table 16 | 188 | 1 min |
| Konjac Gum stock solution | 3001 g | 188 | 3 min |

TABLE 18

Example D Structured Aqueous Composition

| Ingredient | Mass added | Impeller RPM during mixing step | Mixing Time |
|---|---|---|---|
| First Polysaccharide Premix (Table 17) | Sum of Table 17 | 188 | 1 min |
| Xanthan Gum stock solution | 1999 g | 238 | 14 min |

TABLE 19

Freshening Composition

| Ingredient | Mass added | Impeller RPM during mixing step | Mixing Time |
|---|---|---|---|
| Structured Aqueous Composition (Table 18) | Sum of Table 18 | 238 | 1 min |
| Voyager PAC PMC | 925.5 g | 349 | 10 min |
| Silwet L7600 | 100 g | 188 | 3 min |
| Neat pH of Sample | | 5.92 | |

Example E

Example E is an inventive example that demonstrates the preparation of a fabric treatment composition, by an order of addition in which the polysaccharide network is formed after addition of the aqueous ionic content.

Polysaccharides are first dispersed into stock solutions prior to inclusion in the product. Next, an aqueous premix containing the water and majority of the aqueous salts is prepared in the 100 L Mix tank described in FIG. 2. The polysaccharide structure is then added carefully to the aqueous premix, under a prescribed mixing intensity and time. After network formation, the benefit particles are dispersed to a small particle size in the structure at high shear rate. A non-aqueous wetting agent (Silwet) is added in the final step at lower mixing intensity. The total batch Time is 47 minutes.

Preparation of 1 wt % Xanthan Gum Stock Solution 5000 grams of a xanthan gum solution is prepared using the Ytron Y0 high shear mixer. 4946.1 grams of Water is added to a clean mix tank (10 L Glass Beaker). 3.9 grams of Koralone B-119 is added to the beaker, and stirred until homogeneously mixed. 50 grams of xanthan gum are added quickly through the funnel and bypass tube while mixing at 4900 RPM. Mixing at high shear continued for 45 seconds until the powder is completely dispersed.

Preparation of 1 wt % Konjac Gum Stock Solution 5000 grams of a konjac gum solution is prepared using the Ytron Y0 high shear mixer. 4946.1 grams of water is added to a clean mix tank (10 L Glass beaker). 3.9 grams of Koralone B-119 is added to the beaker, and stirred until homogeneously mixed. 50 grams of konjac gum is added quickly through the funnel and bypass tube while mixing at 4900 RPM. Mixing at high shear continued for 45 seconds until the powder is completely dispersed.

Preparation of Aqueous Premix

The mix tank described in FIG. 2 is used to prepare the aqueous premix, and subsequently mix the polysaccharide structure into the aqueous premix. For each step in the aqueous premix making the amount of material, mixing time, and mixing intensity as measured by impeller RPM is listed in Table 20.

Preparation of the First Polysaccharide Premix

Konjac gum stock solution is added to the aqueous premix in the mix tank. The amount of material, mixing time, and mixing intensity as measured by impeller RPM is listed in Table 21.

Preparation of the Structured Aqueous Composition

Xanthan gum stock solution is added to the first polysaccharide premix in the mix tank. The amount of material, mixing time, and mixing intensity as measured by impeller RPM is listed in Table 22.

Preparation of the Freshening Composition

Voyager PAC PMC benefit agent and Silwet L7600 are added to the structured aqueous composition. The amount of material, mixing time, and mixing intensity as measured by impeller RPM is listed in Table 23.

TABLE 20

Example E Aqueous Premix

| Ingredient | Mass added (g) | Impeller RPM during mixing step | Mixing Time |
|---|---|---|---|
| Water | 87928.3 | 188 | 1 min |
| Koralone B-119 | 78.125 | 188 | 1 min |
| Ethanol | 3457.22 | 188 | 2 min |
| Diethylene Glycol | 900.901 | 188 | 1 min |
| Hydroxypropyl Beta CD | 1580.53 | 188 | 2 min |
| Citric Acid | 29.4118 | 188 | 7 min |

TABLE 21

Example E First Polysaccharide Premix

| Ingredient | Mass added | Impeller RPM during mixing step | Mixing Time |
|---|---|---|---|
| Aqueous Premix (Table 20) | Sum of Table 20 | 188 | 1 min |
| Konjac Gum stock solution | 3001 g | 188 | 3 min |

TABLE 22

Example E Structured Aqueous Composition

| Ingredient | Mass added | Impeller RPM during mixing step | Mixing Time |
|---|---|---|---|
| First Polysaccharide Premix (Table 21) | Sum of Table 21 | 188 | 1 min |
| Xanthan Gum stock solution | 1999 g | 238 | 14 min |

TABLE 23

Freshening Composition

| Ingredient | Mass added | Impeller RPM during mixing step | Mixing Time |
|---|---|---|---|
| Structured Aqueous Composition (Table 22) | Sum of Table 22 | 238 | 1 min |
| Voyager PAC PMC | 925.5 g | 349 | 10 min |
| Silwet L7600 | 100 g | 188 | 3 min |

Example F

Example F is an inventive example that demonstrates the preparation of a fabric treatment composition, by an order of addition in which the polysaccharide network is formed after addition of the aqueous ionic content.

Polysaccharides are first dispersed into stock solutions prior to inclusion in the product. Next, an aqueous premix containing the water and majority of the aqueous salts is prepared in the 100 L mix tank described in FIG. 2. The polysaccharide structure is then added carefully to the aqueous premix, under a prescribed mixing intensity and time. After network formation, the benefit particles are dispersed to a small particle size in the structure at high shear rate. A non-aqueous wetting agent (Silwet) is added in the final step at lower mixing intensity. The total batch Time is 74 minutes.

Preparation of 1 wt % Xanthan Gum Stock Solution 5000 grams of a xanthan gum solution is prepared using the Ytron Y0 high shear mixer. 4946.1 grams of water is added to a clean mix tank (10 L glass beaker) 3.9 grams of Koralone B-119 is added to the beaker, and stirred until homogeneously mixed. 50 grams of xanthan gum is added quickly through the funnel and bypass tube while mixing at 4900 RPM. Mixing at high shear continued for 45 seconds until the powder was completely dispersed.

Preparation of 1 wt % Konjac Gum Stock Solution 5000 grams of a konjac gum solution is prepared using the Ytron Y0 high shear mixer. 4946.1 grams of water is added to a clean mix tank (10 L glass beaker). 3.9 grams of Koralone B-119 is added to the beaker, and stirred until homogeneously mixed. 50 grams of konjac gum is added quickly through the funnel and bypass tube while mixing at 4900 RPM. Mixing at high shear is continued for 45 seconds until the powder is completely dispersed.

Preparation of Aqueous Premix

The mix tank illustrated in FIG. 2 is used to prepare the aqueous premix, and subsequently mix the polysaccharide structure into the aqueous premix. For each step in the aqueous premix making the amount of material, mixing time, and mixing intensity as measured by impeller RPM is listed in Table 24.

Preparation of the First Polysaccharide Premix

Konjac gum Stock solution is added to the aqueous premix in the mix tank. The amount of material, mixing time, and mixing intensity as measured by impeller RPM is listed in Table 25.

Preparation of the Structured Aqueous Composition

Xanthan gum stock solution is added to the first polysaccharide premix in the mix tank. The amount of material, mixing time, and mixing intensity as measured by impeller RPM is listed in Table 26.

Preparation of the Freshening Composition

Voyager PAC PMC benefit agent and Silwet L7600 are added to the structured aqueous composition. The amount of material, mixing time, and mixing intensity as measured by impeller RPM is listed in Table 27.

TABLE 24

Example F Aqueous Premix

| Ingredient | Mass added (g) | Impeller RPM during mixing step | Mixing Time |
|---|---|---|---|
| Water | 89279.7 | 188 | 1 min |
| Koralone B-119 | 78.125 | 188 | 1 min |
| Ethanol | 3025.06 | 188 | 2 min |
| Diethylene Glycol | 1301.3 | 188 | 1 min |
| Hydroxypropyl Beta CD | 1128.95 | 188 | 2 min |
| Citric Acid | 58.8235 | 188 | 7 min |

TABLE 25

Example F First Polysaccharide Premix

| Ingredient | Mass added | Impeller RPM during mixing step | Mixing Time |
|---|---|---|---|
| Aqueous Premix (Table 24) | Sum of Table 24 | 188 | 1 min |
| Konjac Gum stock solution | 2405 g | 188 | 3 min |

TABLE 26

Example F Structured Aqueous Composition

| Ingredient | Mass added | Impeller RPM during mixing step | Mixing Time |
|---|---|---|---|
| First Polysaccharide Premix (Table 25) | Sum of Table 25 | 188 | 1 min |
| Xanthan Gum stock solution | 1596 g | 238 | 14 min |

TABLE 27

Freshening Composition

| Ingredient | Mass added | Impeller RPM during mixing step | Mixing Time |
|---|---|---|---|
| Structured Aqueous Composition (Table 26) | Sum of Table 26 | 238 | 1 min |
| Voyager PAC PMC | 1018.05 g | 349 | 10 min |
| Silwet L7600 | 110 g | 188 | 30 min |

Example G

Example G is an inventive example that demonstrates the preparation of a fabric treatment composition, by an order of addition in which the polysaccharide network is formed after addition of the aqueous ionic content.

Polysaccharides are first dispersed into stock solutions prior to inclusion in the product. Next, an aqueous premix containing the water and majority of the aqueous salts is prepared in the 100 L mix tank illustrated in FIG. 2. The polysaccharide structure is then added carefully to the aqueous premix, under a prescribed mixing intensity and time. After network formation, the benefit particles are dispersed to a small particle size in the structure at high shear rate. A non-aqueous wetting agent (Silwet) is added in the final step at lower mixing intensity. The total batch Time is 36 minutes.

Preparation of 1 wt % Xanthan Gum Stock Solution 5000 grams of a xanthan gum solution is prepared using the Ytron Y0 high shear mixer. 4946.1 grams of water is added to a clean mix tank (10 L glass beaker) 3.9 grams of Koralone B-119 is added to the beaker, and stirred until homogeneously mixed. 50 grams of xanthan gum is added quickly through the funnel and bypass tube while mixing at 4900 RPM. Mixing at high shear is continued for 45 seconds until the powder is completely dispersed.

Preparation of 1 wt % Konjac Gum Stock Solution 5000 grams of a konjac gum solution is prepared using the Ytron Y0 high shear mixer. 4946.1 grams of water is added to a clean mix tank (10 L glass beaker). 3.9 grams of Koralone B-119 is added to the beaker, and stirred until homogeneously mixed. 50 grams of konjac gum is added quickly through the funnel and bypass tube while mixing at 4900 RPM. Mixing at high shear is continued for 45 seconds until the powder is completely dispersed.

Preparation of Aqueous Premix

The mix tank described in FIG. 2 was used to prepare the aqueous premix, and subsequently mix the polysaccharide structure into the aqueous premix. For each step in the aqueous premix making the amount of material, mixing time, and mixing intensity as measured by impeller RPM is listed in Table 28.

Preparation of the First Polysaccharide Premix

Konjac gum stock solution is added to the aqueous premix in the mix tank. The amount of material, mixing time, and mixing intensity as measured by impeller RPM is listed in Table 29.

Preparation of the Structured Aqueous Composition

Xanthan gum stock solution is added to the first polysaccharide premix in the mix tank. The amount of material, mixing time, and mixing intensity as measured by impeller RPM is listed in Table 30.

Preparation of the Freshening Composition

Voyager PAC PMC Benefit agent and Silwet L7600 are added to the structured aqueous composition. The amount of material, mixing time, and mixing intensity as measured by impeller RPM is listed in Table 31.

TABLE 28

Example G Aqueous Premix

| Ingredient | Mass added (g) | Impeller RPM during mixing step | Mixing Time |
|---|---|---|---|
| Water | 89226.2 | 188 | 1 min |
| Koralone B-119 | 78.125 | 188 | 1 min |
| Ethanol | 3241.14 | 188 | 2 min |
| Diethylene Glycol | 100.1 | 188 | 1 min |
| Hydroxypropyl Beta CD | 752.634 | 188 | 2 min |
| Citric Acid | 49.0196 | 188 | 7 min |

TABLE 29

Example G First Polysaccharide Premix

| Ingredient | Mass added | Impeller RPM during mixing step | Mixing Time |
|---|---|---|---|
| Aqueous Premix (Table 28) | Sum of Table 28 | 188 | 1 min |
| Konjac Gum stock solution | 3600 g | 241 | 3 min |

TABLE 30

Example G Structured Aqueous Composition

| Ingredient | Mass added | Impeller RPM during mixing step | Mixing Time |
|---|---|---|---|
| First Polysaccharide Premix (Table 29) | Sum of Table 29 | 241 | 1 min |
| Xanthan Gum stock solution | 2400 g | 306 | 5 min |

TABLE 31

Freshening Composition

| Ingredient | Mass added | Impeller RPM during mixing step | Mixing Time |
|---|---|---|---|
| Structured Aqueous Composition (Table 30) | Sum of Table 30 | 306 | 1 min |
| Voyager PAC PMC | 462.75 g | 448 | 10 min |
| Silwet L7600 | 90 g | 400 | 1 min |

Example H

Example H is an Inventive example that demonstrates the preparation of a fabric treatment composition, by an order of addition in which the polysaccharide network is formed after addition of the aqueous ionic content.

Polysaccharides are first dispersed into stock solutions prior to inclusion in the product. Next, an aqueous premix containing the water and majority of the aqueous salts is prepared in the 100 L Mix tank illustrated in FIG. 2. The polysaccharide structure is then added carefully to the aqueous premix, under a prescribed mixing intensity and time. After network formation, the benefit particles are dispersed to a small particle size in the Structure at high shear rate. A non-aqueous wetting agent (Silwet) is added in the final step at lower mixing intensity. The total batch time is 36 minutes.

Preparation of 1 wt % Xanthan Gum Stock Solution 5000 grams of a xanthan gum solution is prepared using the Ytron Y0 high shear mixer. 4946.1 grams of water is added to a clean mix tank (10 L glass beaker) 3.9 grams of Koralone B-119 is added to the beaker and stirred until homogeneously mixed. 50 grams of xanthan gum is added quickly through the funnel and bypass tube while mixing at 4900 RPM. Mixing at high shear is continued for 45 seconds until the powder is completely dispersed.

Preparation of 1 wt % Konjac Gum Stock Solution 5000 grams of a konjac gum solution is prepared using the Ytron Y0 high shear mixer. 4946.1 grams of water is added to a clean mix tank (10 L glass beaker). 3.9 grams of Koralone B-119 is added to the beaker, and stirred until homogeneously mixed. 50 grams of konjac gum is added quickly through the funnel and bypass tube while mixing at 4900 RPM. Mixing at high shear continued for 45 seconds until the powder is completely dispersed.

20 wt % Sodium Chloride Stock Solution 800 grams of a sodium chloride solution is prepared in a 1 L beaker. 640.07 grams of DI water is added to the vessel, and then 160.05 g of sodium chloride. The solution was gently stirred for 2 minutes.

Preparation of Aqueous Premix

The mix tank described in FIG. 2 was used to prepare the aqueous premix, and subsequently mix the polysaccharide structure into the aqueous premix. For each step in the aqueous premix making the amount of material, mixing time, and mixing intensity as measured by impeller RPM is listed in Table 32.

Preparation of the First Polysaccharide Premix

Konjac gum stock solution is added to the aqueous premix in the mix tank. The amount of material, mixing time, and mixing intensity as measured by impeller RPM is listed in Table 33.

Preparation of the Structured Aqueous Composition

Xanthan gum stock solution is added to the first polysaccharide premix in the mix tank. The amount of material, mixing time, and mixing intensity as measured by impeller RPM is listed in Table 34.

Preparation of the Freshening Composition

Voyager PAC PMC Benefit agent and Silwet L7600 is added to the structured aqueous composition. The amount of material, mixing time, and mixing intensity as measured by impeller RPM is listed in Table 35.

TABLE 32

Example H Aqueous Premix

| Ingredient | Mass added (g) | Impeller RPM during mixing step | Mixing Time |
|---|---|---|---|
| Water | 83608.1 | 188 | 1 min |
| Koralone B-119 | 78.125 | 188 | 1 min |
| Ethanol | 3673.29 | 188 | 2 min |
| Diethylene Glycol | 150.15 | 188 | 1 min |
| Hydroxypropyl Beta CD | 1580.53 | 188 | 2 min |
| Citric Acid | 78.4314 | 188 | 7 min |

TABLE 33

Example H First Polysaccharide Premix

| Ingredient | Mass added | Impeller RPM during mixing step | Mixing Time |
|---|---|---|---|
| Aqueous Premix (Table 32) | Sum of Table 32 | 188 | 1 min |
| Konjac Gum stock solution | 6000 g | 241 | 3 min |

TABLE 34

Example H Structured Aqueous Composition

| Ingredient | Mass added | Impeller RPM during mixing step | Mixing Time |
|---|---|---|---|
| First Polysaccharide Premix (Table 33) | Sum of Table 33 | 241 | 1 min |
| Xanthan Gum stock solution | 4000 g | 306 | 5 min |

TABLE 35

Freshening Composition

| Ingredient | Mass added | Impeller RPM during mixing step | Mixing Time |
|---|---|---|---|
| Structured Aqueous Composition (Table 34) | Sum of Table 34 | 306 | 1 min |
| Voyager PAC PMC | 231.4 g | 448 | 10 min |
| Silwet L7600 | 100 g | 188 | 1 min |
| Sodium Chloride (20% stock solution) | 500 g | 188 | 1 min |

Values disclosed herein as ends of ranges are not to be understood as being strictly limited to the exact numerical values recited. Instead, unless otherwise specified, each numerical range is intended to mean both the recited values, any integers within the specified range, and any ranges with the specified range. For example arrange disclosed as "1 to 10" is intended to mean "1, 2, 3, 4, 5, 6, 7, 8, 9, 10."

It should be understood that every maximum numerical limitation given throughout this specification includes every lower numerical limitation, as if such lower numerical limitations were expressly written herein. Every minimum numerical limitation given throughout this specification will include every higher numerical limitation, as if such higher numerical limitations were expressly written herein. Every numerical range given throughout this specification will include every narrower numerical range that falls within such broader numerical range, as if such narrower numerical ranges were all expressly written herein.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

Every document cited herein, including any cross referenced or related patent or application and any patent application or patent to which this application claims priority or benefit thereof, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present disclosure have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A method of manufacturing a freshening composition, the method comprising the steps of:
mixing an aqueous carrier and at least 80 wt. % of ion-forming water-soluble ingredients of the freshening composition to form an aqueous premix, wherein the ion-forming water-soluble ingredients comprise a pH buffer;
subsequently mixing a first polysaccharide into the aqueous premix;
mixing a second polysaccharide into the aqueous premix after mixing the first polysaccharide into the aqueous premix to form a structured aqueous composition; and
dispersing a plurality of particles into the structured aqueous composition to form the freshening composition.

2. The method of claim 1 further comprising the steps of: mixing the first polysaccharide with water to form a first polysaccharide premix prior to the step of mixing the first polysaccharide into the aqueous premix; and mixing the second polysaccharide with water to form a second polysaccharide premix prior to the step of mixing the second polysaccharide into the aqueous premix.

3. The method of claim 1 further comprising the step of introducing a portion of the ion-forming water-soluble ingredients into the structured aqueous composition to lower the viscosity of the structured aqueous composition.

4. The method of claim 1, wherein the aqueous premix, structured aqueous composition, and freshening composition are maintained at a temperature not exceeding 40° C.

5. The method of claim 4, wherein the first and second polysaccharide premixes are maintained at a temperature not exceeding 40° C.

6. The method of claim 1, wherein the ion-forming water-soluble ingredients comprise ingredients selected from the group consisting of: malodor counteractants, preservatives, salts and combinations thereof.

7. The method of claim 1 further comprising the step of adjusting the pH of the aqueous premix to no more than 7 prior to the step of subsequently mixing a first polysaccharide into the aqueous premix.

8. The method of claim 1, wherein the first polysaccharide is xanthan gum, and wherein the second polysaccharide is selected from the group consisting of glucomannan including glucomannan from konjac, locust bean gum, tara gum, and combinations thereof.

9. The method of claim 8, wherein the plurality of particles comprises a plurality of benefit agent delivery particles having a benefit agent and a wall material encapsulating the benefit agent, wherein the benefit agent comprises a material selected from the group consisting of: a perfume mixture, a malodor counteractant, an antimicrobial agent, an insect repellant, and combinations thereof.

10. The method of claim 1, wherein the method produces greater than 100 Kg hr-1 of freshening composition.

11. The method of claim 1, wherein the method is selected from the group consisting of a continuous process, a batch process, or combinations thereof.

12. A method of manufacturing a freshening composition, the method comprising the steps of:
mixing the aqueous carrier and water-soluble ingredients of the freshening composition that comprise a high ionic strength to form an aqueous premix, wherein the water-soluble ingredients comprise a pH buffer;
subsequently mixing a first polysaccharide into the aqueous premix to form a first structured composition;
mixing a second polysaccharide into the aqueous premix after mixing the first polysaccharide into the aqueous premix to form a second structured composition having a yield stress in the range of greater than 0 to about 2,000 mPa and a viscosity in the range of about 2 mPa-s to about 100 mPa-s; and
dispersing a plurality of particles into the structured aqueous composition to form the freshening composition.

13. The method of claim 12 further comprising the step of supplying additional shear energy to the freshening composition, wherein the freshening composition is reduced to a viscosity in the range of about 1 mPa-s to about 20 mPa-s and a yield stress in the range of greater than 0 to about 500 mPa.

14. The method of claim 12 further comprising the step of introducing a portion of the ion-forming water-soluble ingredients into the freshening composition, wherein the freshening composition is reduced to a viscosity in the range of about 1 mPa-s to about 20 mPa-s and a yield stress in the range of greater than 0 to about 500 mPa.

15. The method of claim 12, the aqueous premix, structured aqueous composition, and freshening composition are maintained at a temperature not exceeding 40° C.

16. The method of claim 12 further comprising the step of adjusting the pH of the aqueous premix to no more than 5 prior to the step of subsequently mixing a first polysaccharide into the aqueous premix.

17. The method of claim 12, wherein the first polysaccharide is xanthan gum, and wherein the second polysaccharide is selected from the group consisting of glucomannan including glucomannan from konjac, locust bean gum, tara gum, and combinations thereof.

18. The method of claim 12, wherein the method produces greater than 100 Kg hr-1 of freshening composition, and wherein the method is selected from the group consisting of a continuous process, a batch process, or combinations thereof.

19. A method of manufacturing a freshening composition, the method comprising the steps of:
    mixing an aqueous carrier and ion-forming water-soluble ingredients of the freshening composition in a mix tank, wherein the ion-forming water-soluble ingredients comprise a pH buffer, wherein the mix tank comprises:
        a plurality of baffles, wherein the baffles are defined by a baffle width, an impeller having a plurality of blades, wherein the blades are defined by an impeller width, and a particle injector, wherein the impeller width is about 0.3 to about 0.6 times the tank diameter, wherein the mix tank is defined by a tank height and a tank diameter, wherein the tank height is about 0.8 to about 2.0 times the tank diameter, and wherein the baffle width is about 0.05 to about 0.2 times the impeller width,
    subsequently mixing a first polysaccharide into the aqueous premix;
    mixing a second polysaccharide into the aqueous premix after mixing the first polysaccharide into the aqueous premix to form a structured aqueous composition;
    introducing a plurality of particles adjacent the blades of the impeller to form the freshening composition.

20. The method of claim 19, wherein either the mix tank comprises a high shear rotor stator mixer in the interior of the mix tank or a static mixer is disposed in the exterior of the mix tank.

* * * * *